US007879575B2

(12) United States Patent
Kricka et al.

(10) Patent No.: US 7,879,575 B2
(45) Date of Patent: Feb. 1, 2011

(54) NANOSTRUCTURES THAT PROVIDE A MODIFIED NANOENVIRONMENT FOR THE ENHANCEMENT OF LUMINESCENCE

(75) Inventors: Larry L Kricka, Devon, PA (US); Jason Y Park, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 332 days.

(21) Appl. No.: 11/912,577

(22) PCT Filed: Apr. 26, 2006

(86) PCT No.: PCT/US2006/016245

§ 371 (c)(1),
(2), (4) Date: Mar. 13, 2008

(87) PCT Pub. No.: WO2006/116683

PCT Pub. Date: Nov. 2, 2006

(65) Prior Publication Data

US 2008/0193956 A1    Aug. 14, 2008

Related U.S. Application Data

(60) Provisional application No. 60/675,213, filed on Apr. 27, 2005, provisional application No. 60/736,672, filed on Nov. 15, 2005, provisional application No. 60/782,485, filed on Mar. 15, 2006.

(51) Int. Cl.
   *C12Q 1/66* (2006.01)
(52) U.S. Cl. ........................... 435/8; 435/7.1; 977/745; 977/847
(58) Field of Classification Search .................... 435/8, 435/7.1, 28; 977/745, 847
   See application file for complete search history.

(56) References Cited

U.S. PATENT DOCUMENTS

| | | | |
|---|---|---|---|
| 3,287,324 A | 11/1966 | Sweeny | |
| 3,671,542 A | 6/1972 | Kwolek | |
| 4,598,044 A | 7/1986 | Kricka et al. | |
| 4,678,608 A | 7/1987 | Dugliss | |
| 4,729,950 A | 3/1988 | Kricka et al. | |
| 4,857,652 A | 8/1989 | Schaap | |
| 4,927,769 A | 5/1990 | Chang et al. | |
| 4,931,223 A | 6/1990 | Bronstein et al. | |
| 4,952,707 A | 8/1990 | Edwards et al. | |
| 4,978,614 A | 12/1990 | Bronstein | |
| 5,043,266 A | 8/1991 | Dewar et al. | |
| 5,089,630 A | 2/1992 | Bronstein et al. | |
| 5,112,960 A | 5/1992 | Bronstein et al. | |
| 5,145,772 A | 9/1992 | Voyta et al. | |
| 5,523,212 A | 6/1996 | Akhavan-Tafti et al. | |
| 5,538,847 A | 7/1996 | Bronstein et al. | |
| 5,547,836 A | 8/1996 | Bronstein et al. | |
| 5,552,298 A | 9/1996 | Akhavan-Tafti | |
| 5,578,523 A | 11/1996 | Fiordalice et al. | |
| 5,601,977 A | 2/1997 | Akhavan-Tafti et al. | |
| 5,670,644 A | 9/1997 | Akhavan-Tafti et al. | |
| 5,686,258 A | 11/1997 | Akhavan-Tafti et al. | |
| 5,723,295 A | 3/1998 | Akhavan-Tafti et al. | |
| 5,750,698 A | 5/1998 | Akhavan-Tafti et al. | |
| 5,772,926 A | 6/1998 | Akhavan-Tafti | |
| 5,827,650 A | 10/1998 | Bronstein et al. | |
| 5,840,963 A | 11/1998 | Akhavan-Tafti | |
| 5,849,495 A | 12/1998 | Bronstein et al. | |
| 5,866,045 A | 2/1999 | Akhavan-Tafti et al. | |
| 5,879,894 A | 3/1999 | Law et al. | |
| 5,886,238 A | 3/1999 | Schaap et al. | |
| 5,892,064 A | 4/1999 | Schaap et al. | |
| 5,922,558 A | 7/1999 | Akhavan-Tafti | |
| 5,965,736 A | 10/1999 | Akhavan-Tafti | |
| 6,045,991 A | 4/2000 | Akhavan-Tafti | |
| 6,126,870 A | 10/2000 | Akhavan-Tafti | |
| 6,132,956 A | 10/2000 | Bronstein et al. | |
| 6,139,782 A | 10/2000 | Akhavan-Tafti et al. | |
| 6,180,833 B1 | 1/2001 | Thakur | |
| 6,218,137 B1 | 4/2001 | Akhavan-Tafti et al. | |
| 6,245,928 B1 | 6/2001 | Arghavani et al. | |
| 6,270,695 B1 | 8/2001 | Akhavan-Tafti et al. | |
| 6,284,899 B1 | 9/2001 | Schaap et al. | |
| 6,287,767 B1 | 9/2001 | Bronstein et al. | |
| 6,296,787 B1 | 10/2001 | Akhavan-Tafti et al. | |
| 6,306,610 B1 * | 10/2001 | Bawendi et al. | ............. 435/7.1 |
| 6,346,615 B1 | 2/2002 | Bronstein et al. | |
| 6,353,129 B1 | 3/2002 | Akhavan-Tafti et al. | |
| 6,362,011 B1 | 3/2002 | Massey et al. | |
| 6,410,732 B2 | 6/2002 | Akhavan-Tafti et al. | |
| 6,410,751 B1 | 6/2002 | Akhavan-Tafti et al. | |
| 6,544,732 B1 * | 4/2003 | Chee et al. | .................... 435/6 |
| 6,635,437 B2 | 10/2003 | Akhavan-Tafti et al. | |

(Continued)

OTHER PUBLICATIONS

Yin X. et al. 4-(Dimethylamino)butyric Acid Labeling for Electrochemiluminescence Detection . . . Analytical Chemistry 77(11)3525-3530, Jun. 1, 2005.*

Baldwin et al., "Cloning and Expression of the *luxY* Gene from *Vibro fischeri* Strain Y-1 in *Escherichia coli* and Complete Amino Acid Sequence of the Yellow Fluorescent Protein," *Biochemistry* 1990; 29:5509-5515.

Boute et al., "The Use of Resonance Energy Transfer in High-Throughput Screening: BRET versus FRET," *Trends in Pharmacological Sciences* 2002; 23:351-354.

(Continued)

*Primary Examiner*—Ralph Gitomer
(74) *Attorney, Agent, or Firm*—Woodcock Washburn, LLP

(57) ABSTRACT

The present invention relates to nanostructures for use in luminescent assays as well as methods for the production of nano-sized tube and rods, including arrays of nanotubes and nanorods from a nylon.

55 Claims, 19 Drawing Sheets

U.S. PATENT DOCUMENTS

| | | | |
|---|---|---|---|
| 6,696,569 | B2 | 2/2004 | Akhavan-Tafti et al. |
| 6,958,381 | B2 | 10/2005 | Winterling et al. |
| 2003/0077599 | A1* | 4/2003 | Sogard .......................... 435/6 |
| 2003/0155560 | A1 | 8/2003 | Palmer et al. |
| 2008/0286856 | A1* | 11/2008 | Park et al. ................. 435/283.1 |
| 2009/0196826 | A1* | 8/2009 | Gao et al. ..................... 424/9.3 |
| 2009/0263914 | A1* | 10/2009 | Pettersson ................... 436/501 |

OTHER PUBLICATIONS

Bronstein et al. "1,2-Dioxetanes: Novel Chemiluminescent Enzyme Substrates. Applications to Immunoassays," *J Biolumin Chemilumin* 1989;4:99-111.

Bronstein et al., "Chemiluminescent Reporter Gene Assays: Sensitive Detection of the GUS and SEAP Gene Products," *Biotechniques* 1994;17:172-4, 176-7.

Heid CA et al., "Real Time Quantitative PCR," *Genome Research.* 1996;6:986-94.

Issad et al., "A Homogenous Assay to Monitor the Activity of the Insulin Receptor Using Bioluminescence Resonance Energy Transfer," *Biochemical Pharmacology* 2002;64:813-817.

Jones, S. G. et al., "Improvements in the Sensitivity of Time Resolved Fluorescence Energy Transfer Assays," *J. Fluorescence* 2001;11, 13-21.

Kricka, *Ligand-binder assays*, New York: Dekker, 1985.

Lakowicz et al., "Radioactive Decay Engineering," *Anal Biochem.* 2002; 301: 261-277.

Lakowicz et al., "Intrinsic Fluorescence from DNA Can be Enhanced by Metallic Particles," *Biochem Biophys Res Commun* 2001; 286: 875-879.

Levine et al., "Isolation and characterization of a photoprotein, "Phialidin", and a spectrally unique green-fluorescent protein from the bioluminescent jellyfish *Phialidium gregarium*," *Comp. Biochem. Physiol.*, 1982; 72B:77-85.

Li, M. and Selvin, "Amine-Reactive Forms of a Luminescent Diethylenetriaminepentaacetic Acid Chelate of Terbium and Europium: Attachment to DNA and Energy Transfer Measurements," P. R. *Bioconjug. Chem.*, 1997; 8, 127-132.

Lvov et al., "Direct Electrochemistry of Myoglobin and Cytochrome P450 in Alternate Layer-by-Layer Films with DNA and Other Polyions," *J. Am. Chem. Soc.* 1998, 120, 4073-80.

Milligan G., "Applications of Bioluminescence- and Fluorescence Resonance Energy Transfer to Drug Discovery at G Protein-Coupled Receptors," *European Journal of Pharmaceutical Sciences.* 2004; 21(4):397-405.

Norris et al., "Nucleotide Sequence of a cDNA Clone Encoding the Precursor of the Peridinin-Chlorophyl α-Binding Protein from the Dinoflagellate Symbiodinium sp." *Plant Molecular Biology* 1994; 24:673:77.

Parsons M. Vojnovic B. Ameer-Beg S., "Imaging Protein- Protein Interactions in Cell Motility Using Fluorescence Resonance Energy Transfer (FRET)," *Biochemical Society Transactions.* 2004;32:431-3.

Pastorino, et al., "Complex Catalytic Colloids on the Basis of Firefly Luciferase as Optical Nanosensor Platform," *Biotechnology and Bioengineering* 2003, 84, 286-91.

Rolinski et al., "Sensing Metabolites Using Donor-Acceptor Nanodistributions in Fluorescence Resonance Energy Transfer," *Appl Phys Lett* 2001;78 (18) :2796-8.

Rouse & Lillehei, "Electrostatic Assembly of Polymer/Single Walled Carbon Nanotube Multilayer Films," *Nano Letters* 2003, 3, 59-62.

Schuurs and van Weemen, "Enzyme-immunoassay: a powerful analytical tool," *J Immunoassay* 1980;1: 229-49.

Weihong Tan et al., "Molecular Beacons," *Current Opinion in Chemical Biology.*2004; 8(5):547-53.

Truong K. Ikura M., "The Use of FRET Imaging Microscopy to Detect Protein- Protein Interactions and Protein Conformational Changes in vivo," *Current Opinion in Structural Biology.* 2001;11:573-8.

Wang et al., "Peptides with Selective Affinity for Carbon Nanotubes," *Nature Materials* 2003 2: 196-200.

Ward et al., "Spectral Perturbations of the *Aequorea* Green-Fluorescent Protein," *Photochem. Photobiol.* 1982; 35:803-808.

Wu P, Brand L., "Resonance Energy Transfer: Methods and Applications," *Anal Biochem* 1994;218:1-13.

Yanlong Li et al., "Design, Synthesis, and Spectroscopic Properties of Peptide-Bridged Fluorescence Energy-Transfer Cassettes," *Bioconjug. Chem.* 1999;10: 241-245.

Tonucci, R.J. et al., "Nanochannel Array Glass," *Science*, Oct. 30, 1992, 258, 783-785.

Azamian et al., "Bioelectrochemical Single-Walled Carbon Nanotubes," *J. Am. Chem. Soc.*, 2002, 124, 12664-5.

Baskaran, D. et al., "Polymer-Grafted Multiwalled Carbon Nanotubes through Surface-Initiated Polymerization," *Agnew Chem. Int.*, 2004, 43, 2138-2142.

Cepak, V.M. et al., "Fabrication and characterization of concentric-tubular composite micro- and nanostructures using the template-synthesis method," *J. Mater. Res..*, 1998, 13, 3070-3080.

Chen et al., "Noncovalent Sidewall Functionalization of Single-Walled Carbon Nanotubes for Protein Immobilization," *J. Am. Chem. Soc.*, 2001, 123, 3838-9.

Chen et al., "Solution Properties of Single-Walled Carbon Nanotubes," *Science*, 1998, 282(5386), 95-98.

Colquoun, H.M. et al., "Microfabrication of High-performance aromatic polymers as nanotubes or fibrils by in situ ring-opening polymerization of macrocyclic precursors," *J. Mater. Chem.*, 2003, 13, 1504-1506.

E.F. Ullman, M. Schwarzberg, K.E. Rubenstein, "Fluorescent Excitation Transfer Immunoassay," *J. Biol. Chem.* 1976; 251(14): 4172-4178.

Erlanger, B.F. et al., "Binding of an Anti-Fullerene IgG Monclonal Antibody to Single Wall Carbon Nanotubes," *Nano Letts*, 2001, 1, 465-7.

Ghadiri, M.R. et al., "Self-assembling organic nanotubes based on a cyclic peptide architecture," *Nature*, 1993, 366, 424-7.

Grumelard, J. et al., "Soft nanotubes from amphiphillic ABA tribloc macromonomers," *Chem. Commun.*, 2004, 13, 1462-3.

Hulteen et al., "A general template-based method for the preparation of nanomaterials," *J. Mater. Chem.*, 1997, 7, 1075-1087.

Kricka, L.J. et al., "Effect of Solvents on the Catalytic Activity of Firefly Luciferase,", *Arch. Biophys.*, 1982, 217, 674-80.

Lee et al., "Antibody-Based Bio-Nanotube Membranes for Enantiomeric Drug Separations," *Science*, Jun. 21, 2002, 296, 2198-2200.

Mamedov, et al, "Molecular Design of Strong Single-Wall Carbon Nanotube/Polyelectrolyte Multilayer Composites," *Nature Materials* 2002, 1, 190-4.

Martin, C.R., Nanomaterials: A Membrane-Based Synthetic Approach, *Science*, 1994, 266, 1961-1966.

Martinek, K. et al., "Micellar enzymology," *Eur. J. Biochem.*, 1986, 155, 453-68.

Mitchell, D.T. et al., "Smart Nanotubes for Bioseparations and Biocatalysis," *J. Am. Chem. Soc.*, 2002, 124, 11864-5.

N. Ota, et al., "Determination of Interactions Between Structured Nucleic Acids by Fluorescence Resonance Energy Transfer (FRET): Selection of Target Sites for Functional Nucleic Acids," *Nucleic Acid Res.* 26 (3) (1998) 735-743.

Nagase, H. et al., "Design and Characterization of a Fluorogenic Substrate Selectively Hydrolyzed by Stromelysin 1 (Matrix Metalloproteinase-3)," *J. Biol. Chem.*, 1994;269, 20952-20957.

Nicewarner, S.R. et al., "Submicrometer Metallic Barcodes," *Science*, 2001, 294, 137-141.

Patel, L. R. et al. "Energy Transfer Analysis of Fos-Jun Dimerization and DNA Binding," *Proc. Natl. Acad. Sci. USA*, 1994;91;7360-7364.

Tyagi, S. et al., "Molecular Beacons: Probes that Fluoresce upon Hybridization," *Nat. Biotechnol.* 1996;14 :303-308.

Shim, M. et al., "Functionalization of Carbon Nanotubes for Biocompatibility and Biomolecular Recognition," *Nano Letts*, 2002, 2, 285-282.

Ya-Ping Sun et al., "Functionalized Carbon Nanotubes: Properties and Applications," *Acc. Chem. Res.*, 2002, 35, 1096-1104.

Wang et al., "Ultrasensitive Electrical Biosensing of proteins an DNA: Carbon-nanotube derived amplification of the recognition and transduction events," *J. Am. Chem. Soc.*, 2004, 126, 3010-1.

Ward, W.W. et al., "Extraction of Renilla-Type Luciferin from the Calcium-Activated Photoproteins Aequorin, Mnemiopsin, and Berovin," *Proc. Natl. Acad. Sci. USA*, Jul. 1975, 72(7), 2530-2534.

Whitesides, G.M. et al., "Molecular Self-Assembly and Nanochemistry: A Chemical Strategy for the Synthesis of Nanostructures," *Science*, Nov. 29, 1991, 254(5036), 1312-1319.

Wilbanks et al., "Rod Structure of a Phycoerythrin II-Containing Phycobilisome," *J. Biol. Chem.* 1993; 268:1226-35.

Wong, S. S. et al., "Covalently functionalized nanotubes as nanometer-sized probes in chemistry and biology," *Nature*, 1998, 394, 52-55.

Zheng et al., "Structure-Based Carbon Nanotube Sorting by Sequence-Dependent DNA Assembly," *Science* 2003; 302: 1545-1548.

* cited by examiner

NANOSTRUCTURES THAT PROVIDE A MODIFIED NANOENVIRONMENT FOR THE ENHANCEMENT OF LUMINESCENCE

CROSS-REFERENCE TO RELATED APPLICATIONS

This application is the National Stage of International Application No. PCT/US2006/016245 filed Apr. 26, 2006, which claims the benefit of U.S. Provisional Application No. 60/675,213, filed Apr. 27, 2005; U.S. Provisional Application No. 60/736,672, filed Nov. 15, 2005; and U.S. Provisional Application No. 60/782,485, filed Mar. 15, 2006, the disclosures of which are incorporated herein by reference in their entireties.

FIELD

The present invention relates to nanostructures for use in luminescent assays as well as methods for the production of nano-sized tube and rods, including arrays of nanotubes and nanorods from a nylon.

BACKGROUND

Enzymes are widely used as labels in immunoassay and in nucleic acid testing as labels. The catalytic activity of an enzyme can provide inherent signal amplification since one enzyme molecule can turn over many substrate molecules to produce a detectable product. The two most commonly used labels are alkaline phosphatase and horseradish peroxidase.

The enzymes alkaline phosphatase and horseradish peroxidase have been used as labels in immunohistochemistry and in immunoassays for over 30 years. Various methods are available to detect and measure the activity of alkaline phosphatase and horseradish peroxidase based on the generation of soluble and insoluble colored products, fluorescent products, and chemi-and bioluminescent products (Kricka, *Ligand-binder assays*, New York: Dekker, 1985; Schuurs and van Weemen, *J Immunoassay* 1980;1:229-49).

Chemiluminescent assays based on adamantyl 1,2-dioxetane aryl phosphates are one of the principal types of assays for detecting and measuring the activity of alkaline phosphatase. They are widely used in high throughput clinical immunoassay analyzers and commercial Western blotting kits for proteins and Southern and Northern blotting kits for nucleic acids. Alkaline phosphatase cleaves the phosphate group to produce an unstable phenoxide. This decomposes via scission of the 1,2-dioxetane ring to produce adamantanone and a fluorescent phenoxy ester in an electronically excited state. The latter intermediate decays to the electronic ground state and the excess energy is emitted as a glow of light (Bronstein et al. *J Biolumin Chemilumin* 1989;4:99-111). It should be appreciated that the chemiluminescent 1,2-dioxetane type of reaction used to measure alkaline phosphatase is less than ten percent efficient. Ninety percent of the substrate that reacts with the enzyme does not produce a light signal. Any means of improving the light producing efficiency of this reaction would be rewarded in improvements in the detection limit for alkaline phosphatase and this would translate into improved sensitivity for assays using this label.

Chemiluminescent assays based on the luminol reaction enhanced by phenols are one of the principal types of assays for detecting and measuring the activity of horseradish peroxidase and are widely used in high throughput routine clinical immunoassay analyzers and commercial Western blotting kits for proteins and Southern and Northern blotting kits for nucleic acids.

The chemiluminescent luminol reaction used to measure peroxidase is less than one percent efficient. Ninety-nine percent of the substrate that reacts with the enzyme does not produce a light signal. Any means of improving the light producing efficiency of this reaction would be rewarded in improvements in the detection limit for horseradish peroxidase and this would translate into improved sensitivity for assays using this label.

The gene for firefly luciferase has become important as a reporter gene (Bronstein et al., *Biotechniques* 1994;17:172-4, 176-7), and gene expression is assessed by measuring the activity of the expressed firefly luciferase using a mixture of Mg-ATP and firefly luciferin. The reaction of firefly luciferase with firefly luciferin is the most efficient bioluminescent reaction known and the quantum yield has been estimated to approach 100%. A feature of this bioluminescent reaction is that the product, oxyluciferin, is an inhibitor of the enzyme, and thus it only turns over a few times before becoming inactivated. This, together with the difficulty encountered in attaching antigen and antibodies to the very hydrophobic luciferase, has limited the use of this enzyme as a label. A means for improving the turn-over of this enzyme would be rewarded in improvements in the detection limit for luciferase.

As will be appreciated, there are many other compounds that can be used to generate luminescence in luminescent assay systems. The full potential of these compounds remains unrealized. A need exists for improving the efficiency of luminescent assays. The present invention is directed to this, as well as other, important ends.

SUMMARY

Nanostructures for Use in Luminescent Assays

Figure 1:
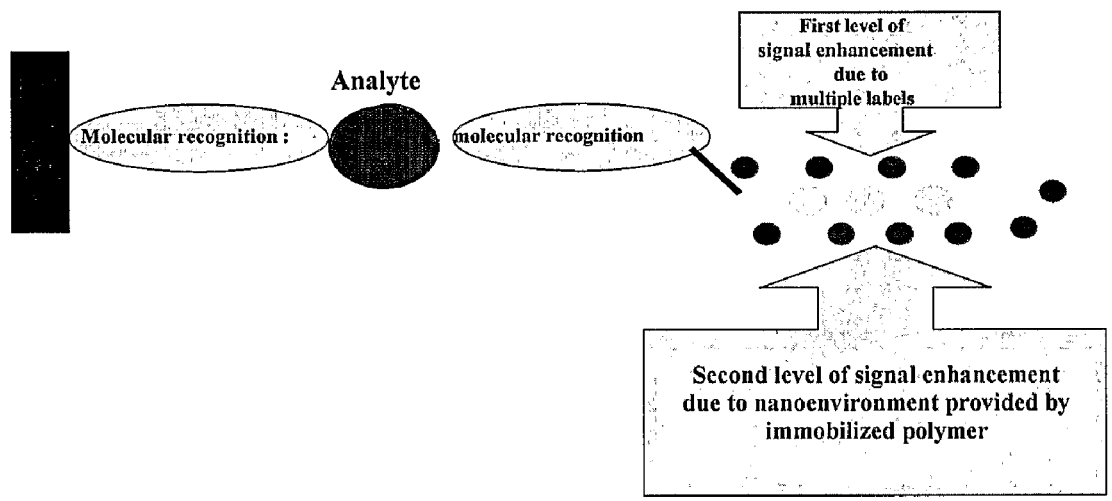
FIG. 1 is a schematic showing the application of an enzyme-polymer nanotube in a two-site capture assay illustrating two sources of signal enhancement.
Figure 2:
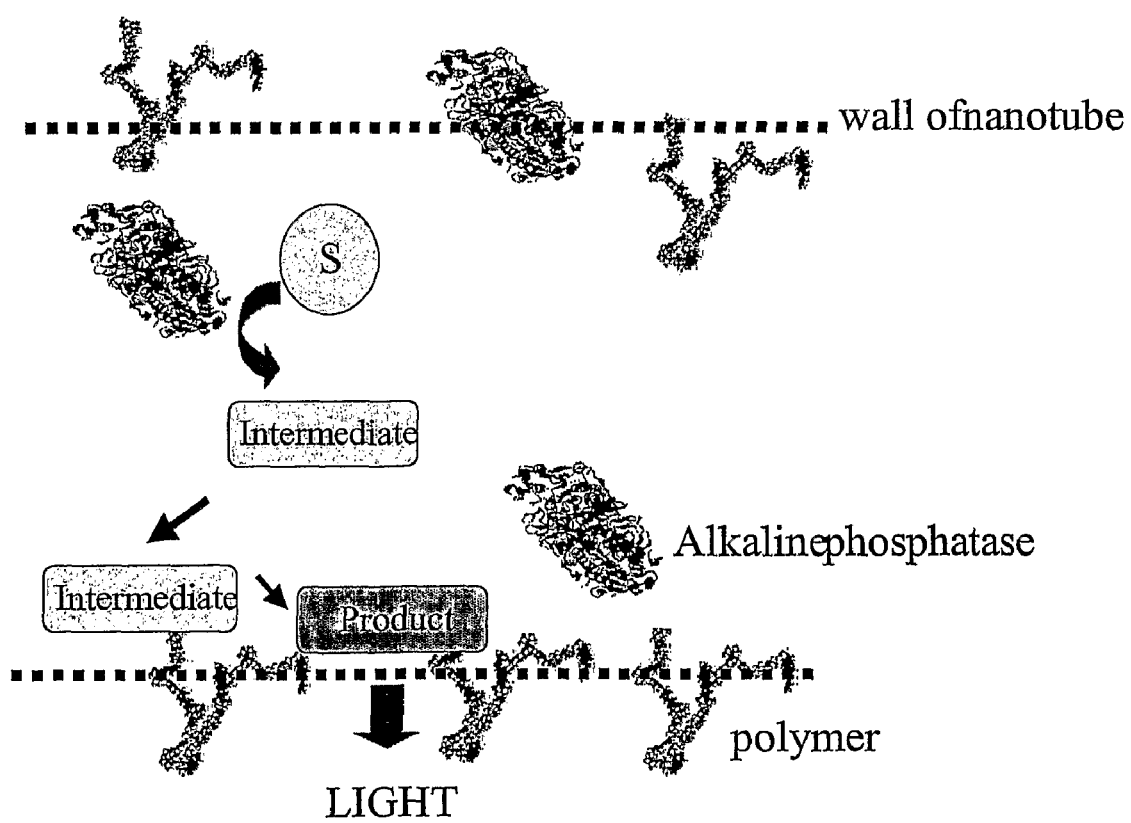
FIG. 2 is a schematic of enhancement of exemplary chemiluminescent assay for alkaline phosphatase labels immobilized-in a nanotube by a nanoenvironment created by polymer immobilized on the nanotube.
Figure 3:
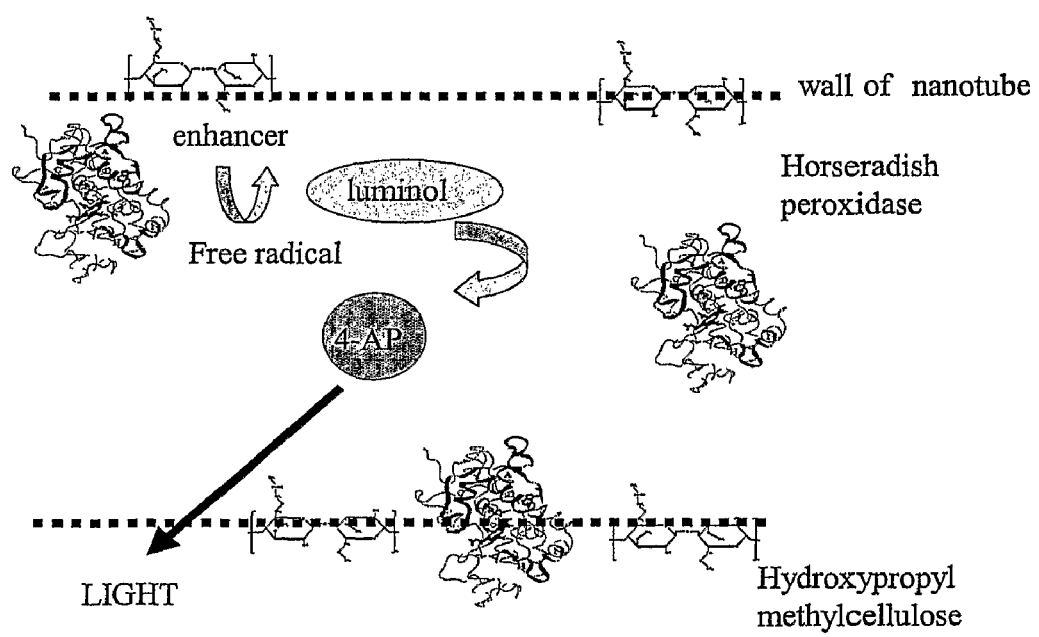
FIG. 3 is a schematic of enhancement of exemplary chemiluminescent assay for horseradish peroxidase labels immobilized in a nanotube by a nanoenvironment created by polymer immobilized on the nanotube.
Figure 4:
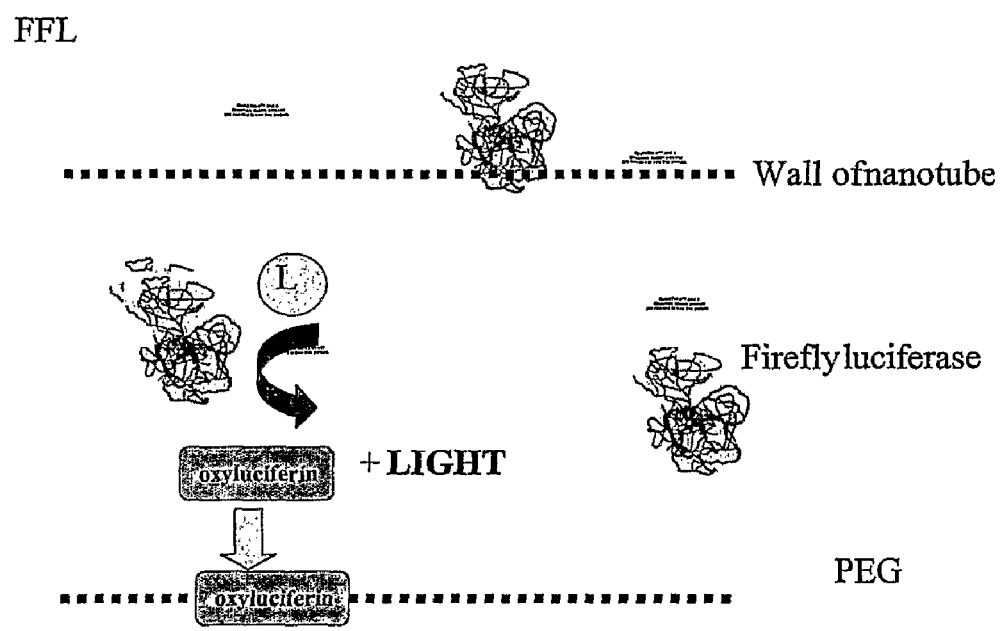
FIG. 4 is a schematic of enhancement of exemplary bioluminescent assay for firefly luciferase labels immobilized in a nanotube by a nanoenvironment created by polymer immobilized on the nanotube.
Figure 5:
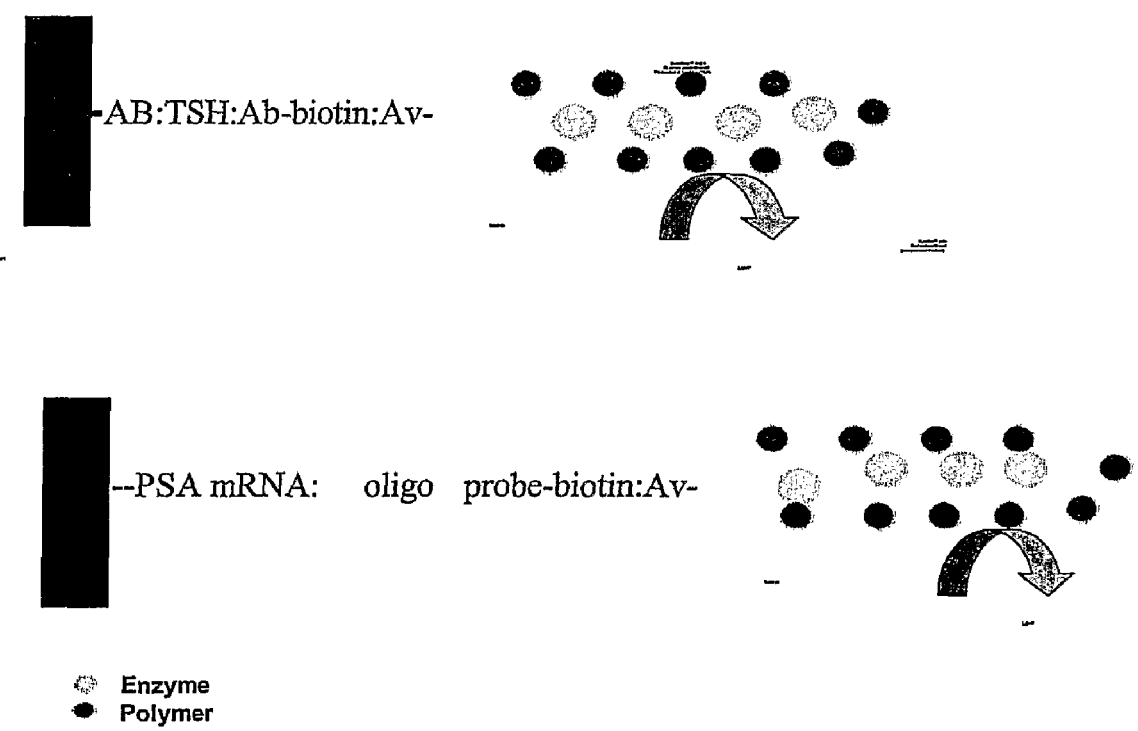
FIG. 5 is a schematic of application of enzyme polymer nanotubes in an immunoassay for TSH (A) and PSA mRNA (or cDNA) (B).
Figure 6:
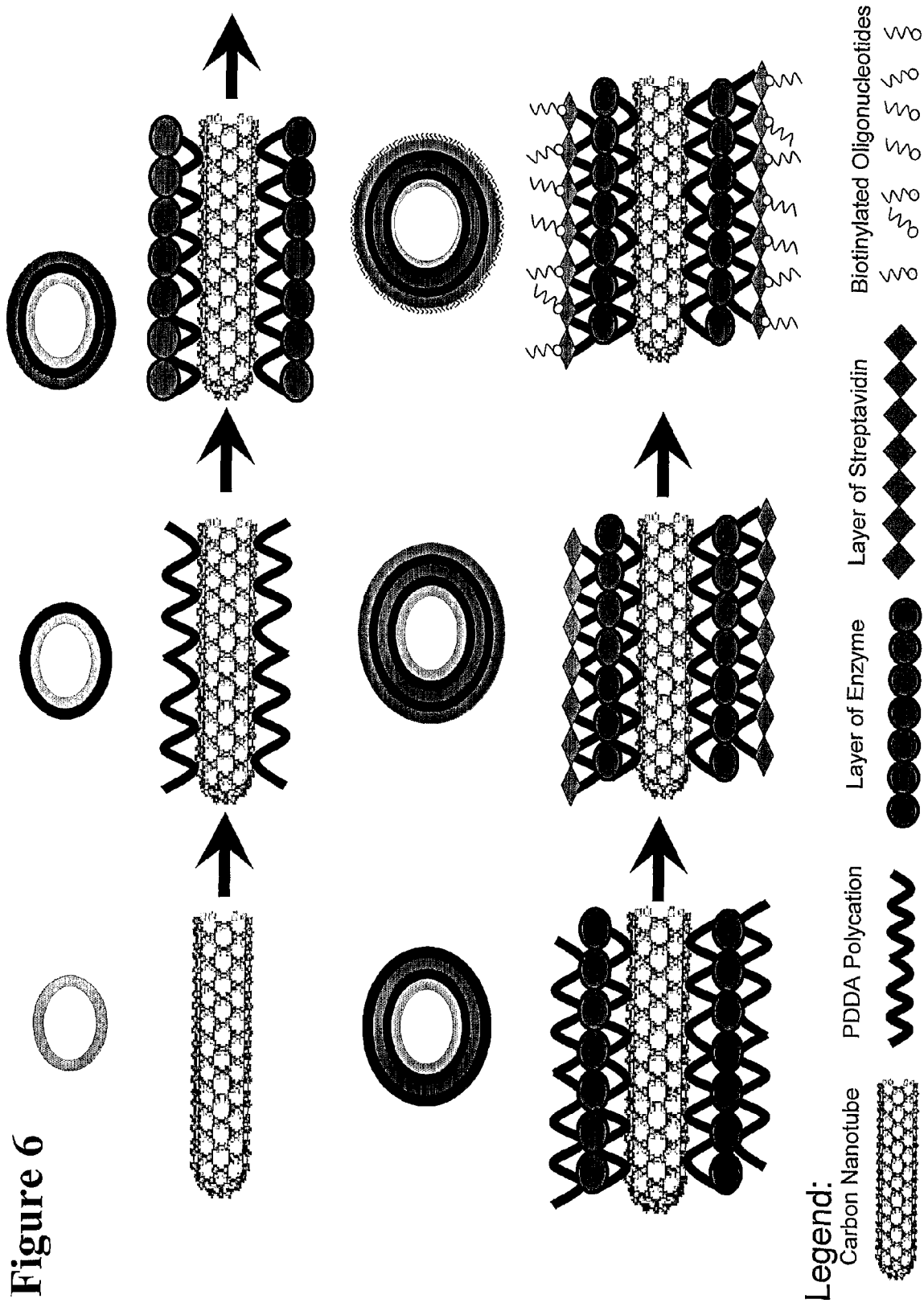
FIG. 6 demonstrates one example of layer-by-layer assembly of polymer on a nanotube. Carboxylated carbon nanotubes are absorbed with alternative layers of polymer and enzyme. The structure is capped with an outermost layer of polymer. This enzyme packed carbon nanotube is modified with streptavidin to be attached to any number of nucleic acid or protein ligands.
Figure 7:
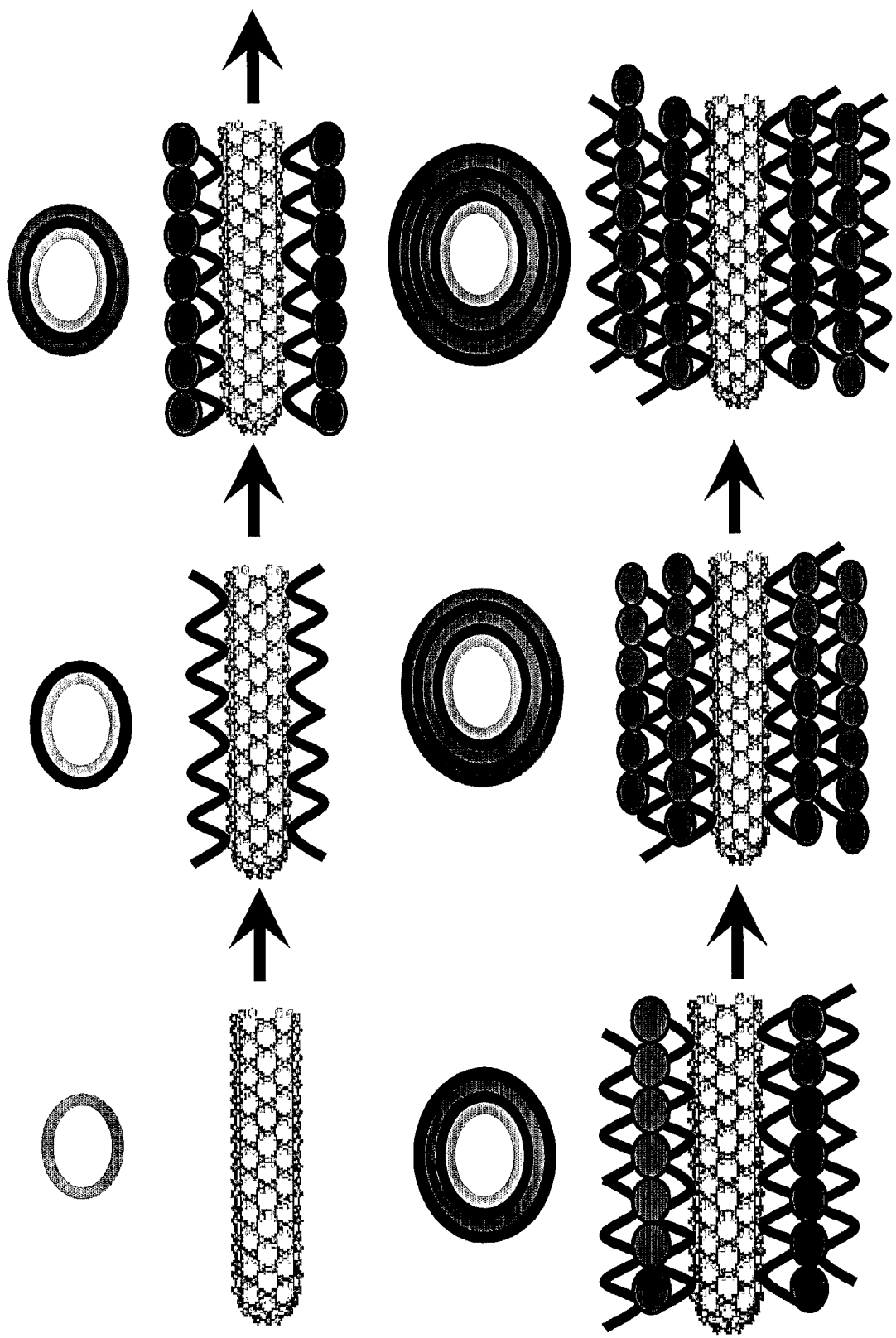
FIG. 7 demonstrates that multiple layers of polymer can be assembled on the nanostructure.
Figure 8:
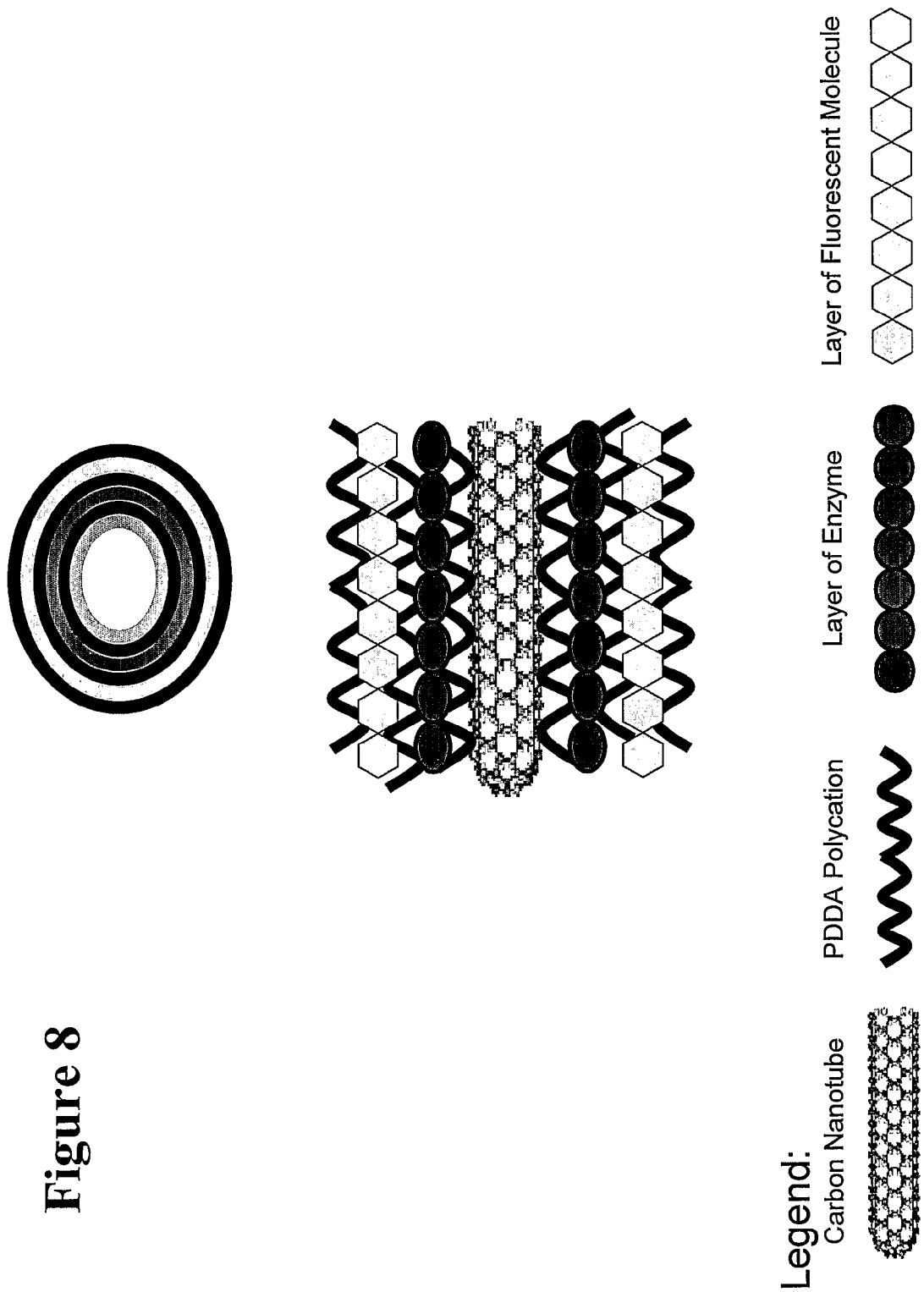
FIG. 8 demonstrates that the layer-by-layer technique can be used to fabricate nanostructures having fluorescent labels adjacent to chemiluminescent labels.
Figure 9:
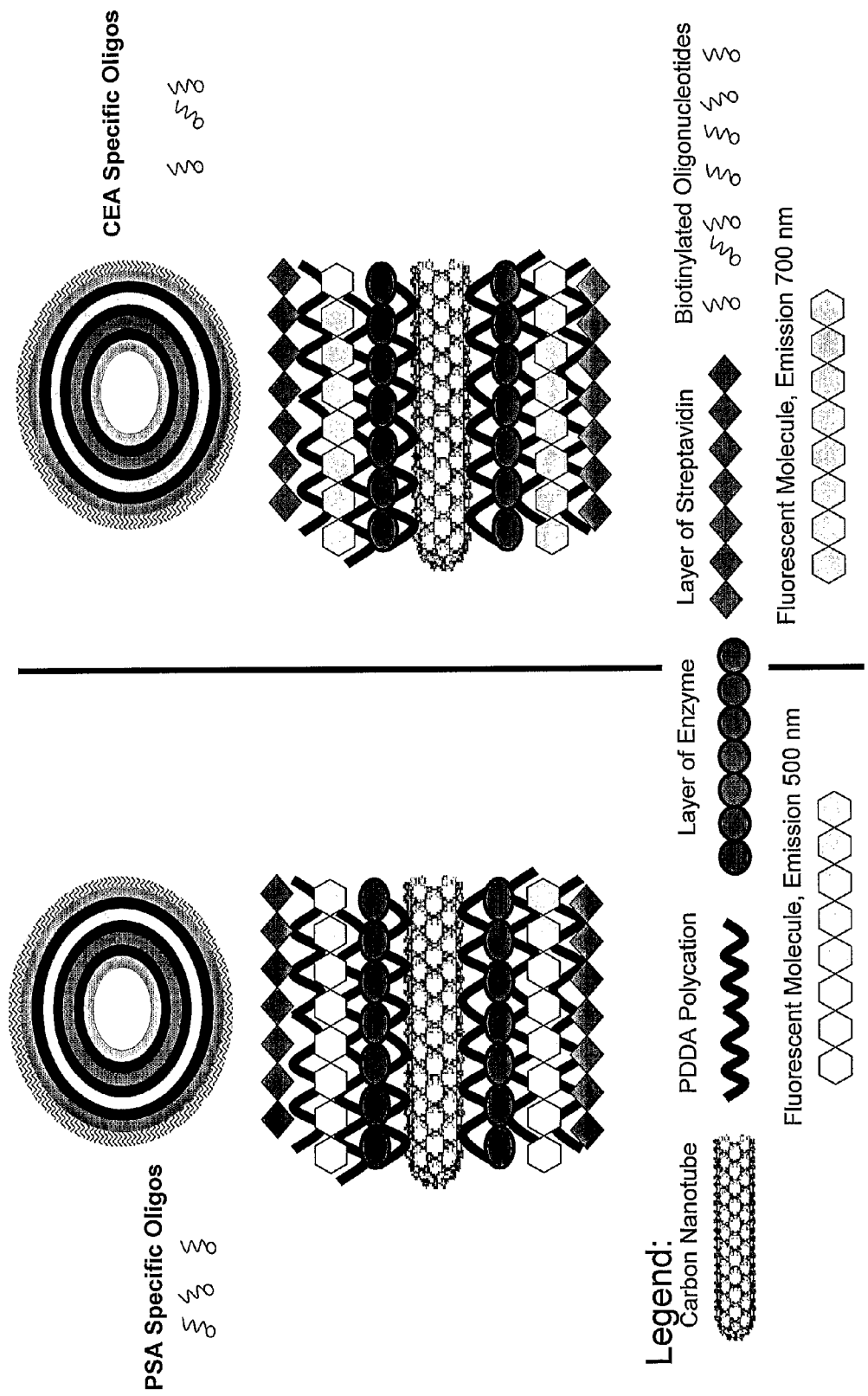
FIGS. 9A & 9B demonstrate an exemplary assay system that uses multiple types of layer-by-layer nanostructures, each of which contains the same chemiluminescent enzyme, but a different fluorescent molecule: 9A depicts an assay system that uses a fluorescent molecule with 500 nm emission, while the assay system in 9B uses a fluorescent molecule with 700 nm emission.
Figure 10:
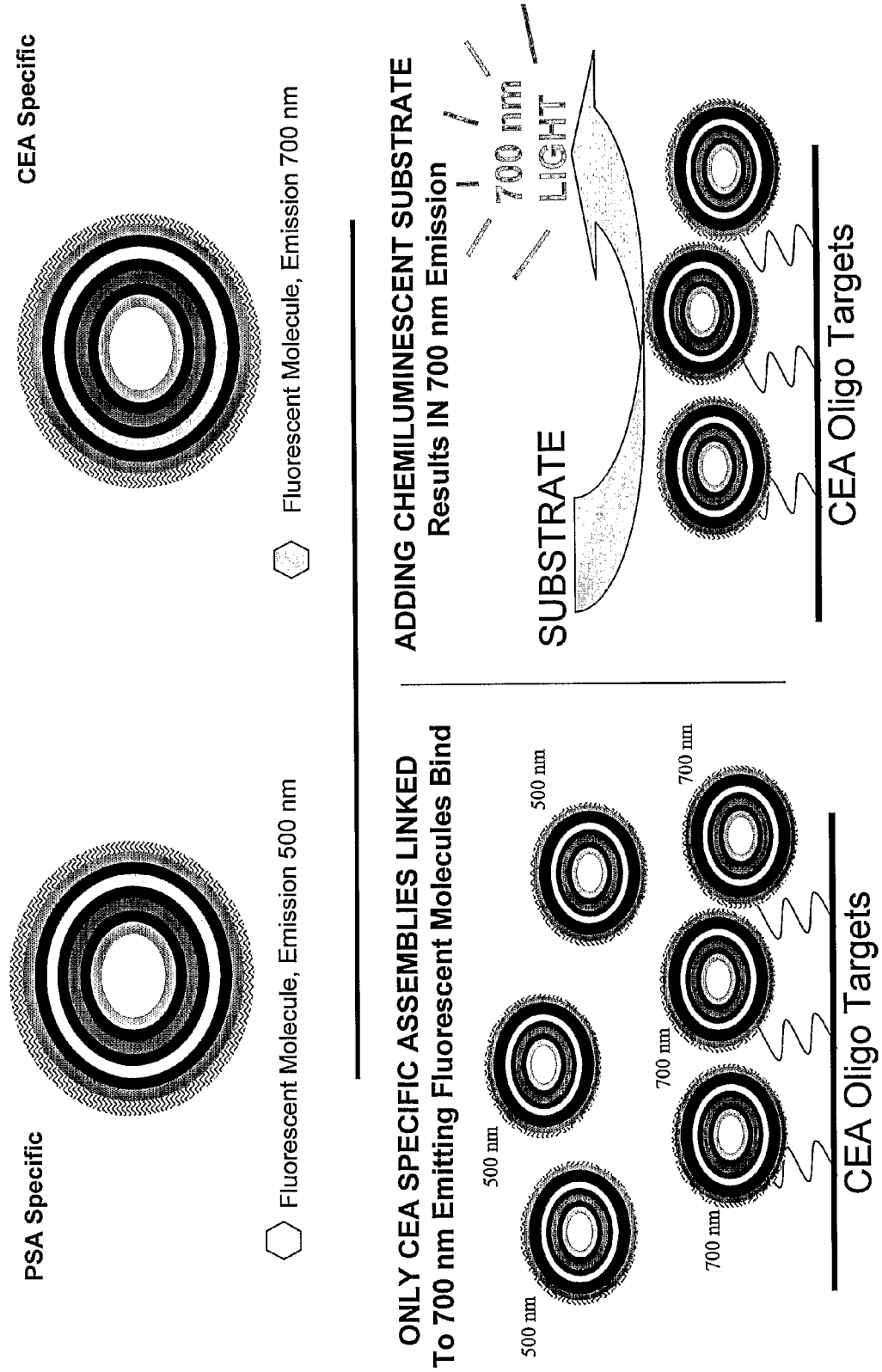
FIG. 10 demonstrates an exemplary capture type assay where each analyte of interest is associated with a different fluorescent molecule. The detection of a specific fluorescent molecule indicates the presence of a specific analyte.
Figure 11:
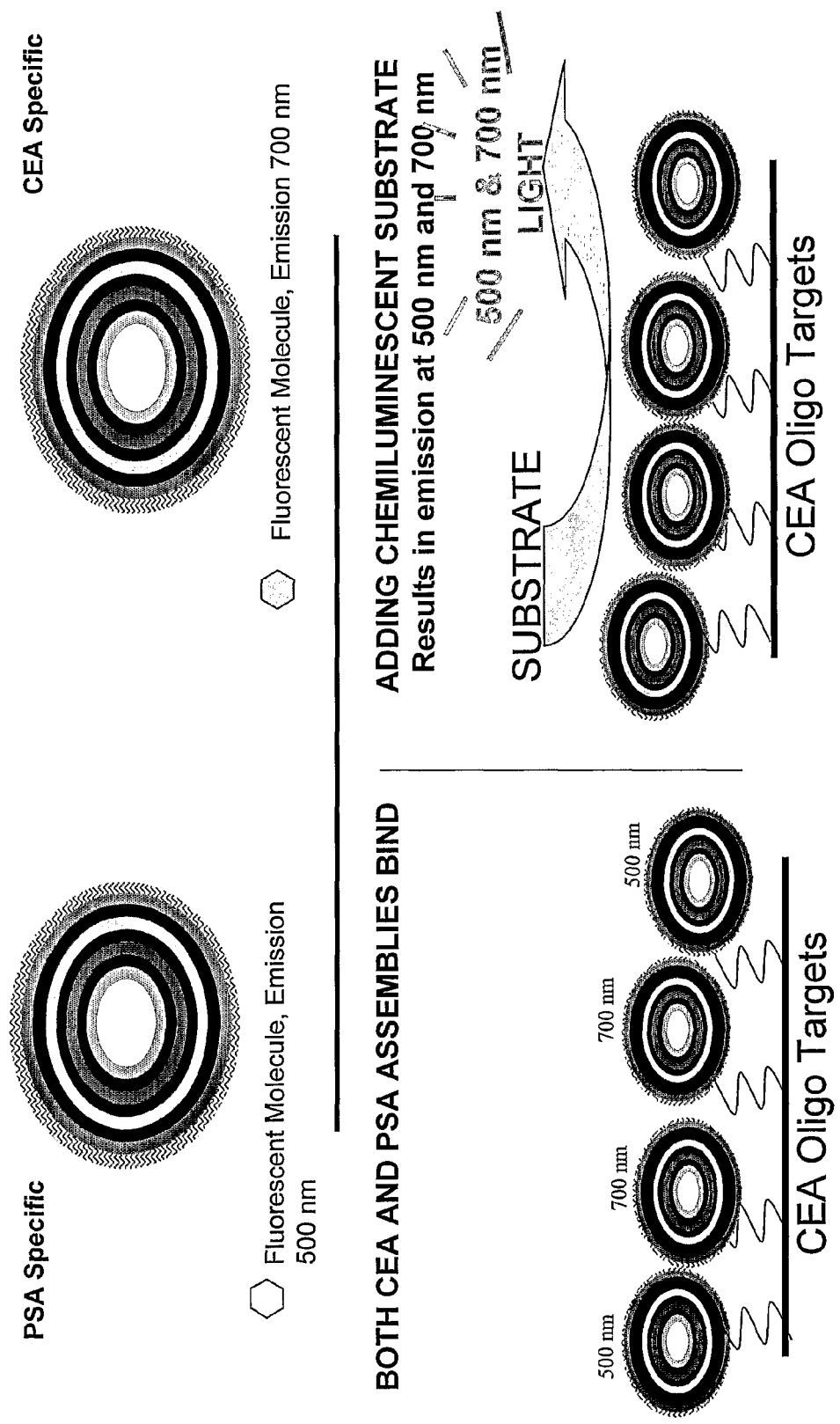
FIG. 11 demonstrates an exemplary capture type assay designed to simultaneously detect multiple analytes.
Figure 12:
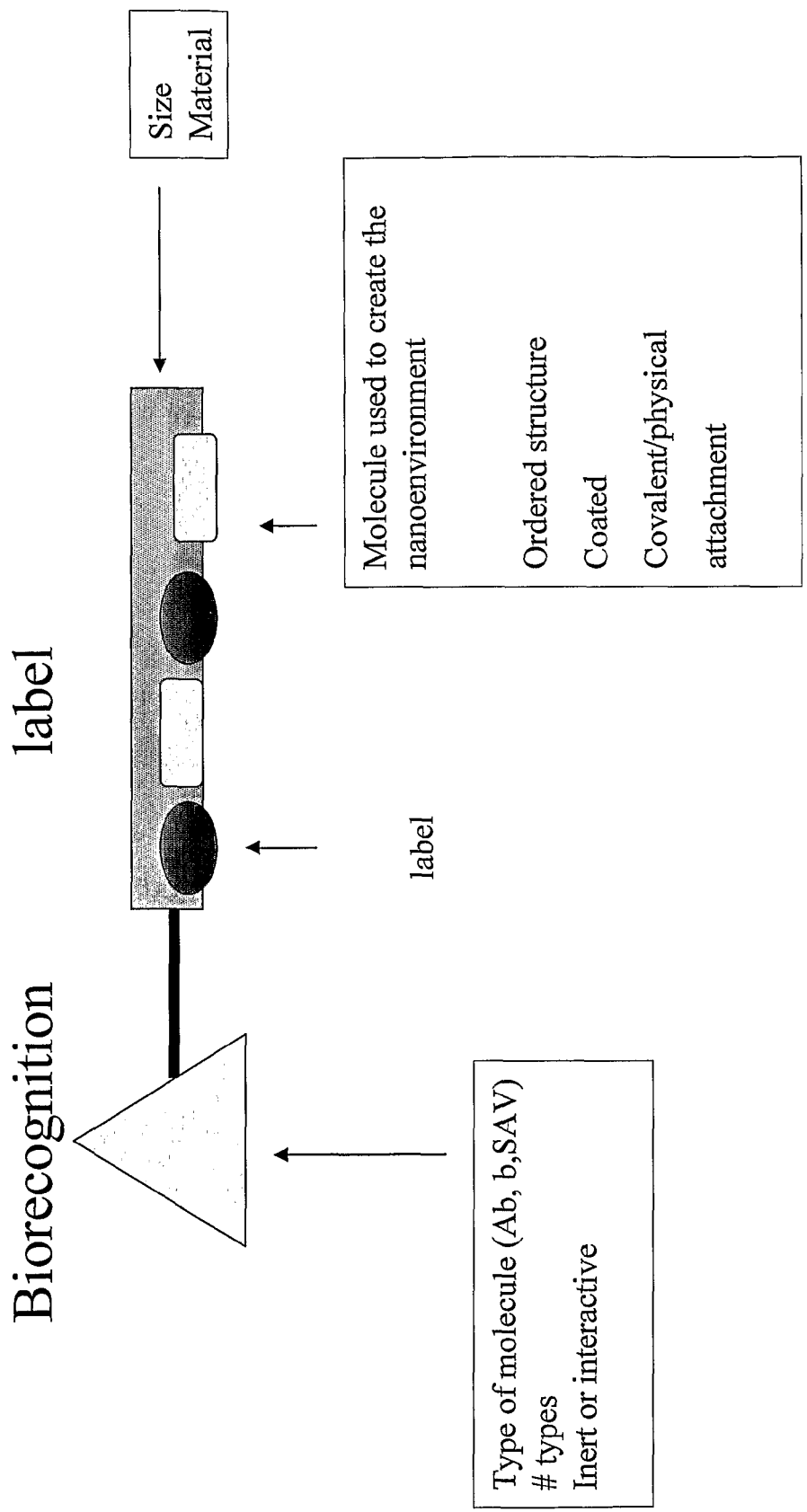
FIG. 12 provides an exemplary scheme of the juxtaposition of a label and molecule used to create a nanoenvironment that is conducive to the signal produced by the label. The label and molecule are placed as an ordered immobilized structure so as to create an ordered nanoenvironment on a nanosized substrate, e.g. a nanotube. This contrasts with the random interactions that would occur if both or either were free in solution.
Figure 13:
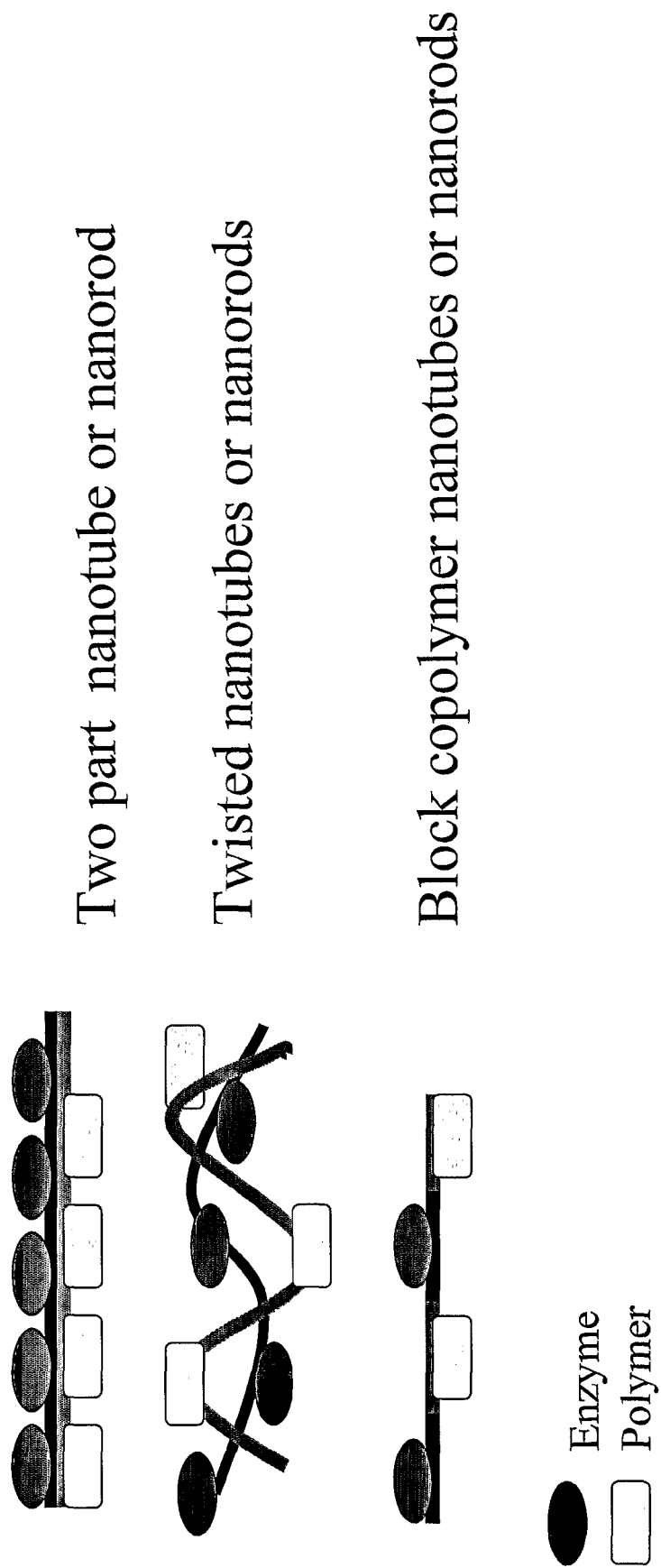
FIG. 13 provides an exemplary scheme of the juxtaposition of a label and molecule used to create a nanoenvironment that is conducive to the signal produced by the label based on the use of nanofibers. A laminated nanofiber is created from two dissimilar materials. One material will bind to the label and the other to the molecule used to create a nanoenvironment. Adsorption of the two different types of molecules leads to an ordered structure in which the two types of molecule are in juxtaposition. An ordered structure in which the two types of molecule are in juxtaposition can also be achieved by twisting together two fibers made from two dissimilar materials. One material will bind to the label and the other to the molecule used to create a nanoenvironment by virtue of the juxtaposition of the molecules immobilized on the different structures. An ordered structure in which the two types of molecule are in juxtaposition can also be achieved by creating a block copolymer in which one block (formed from monomer 1) binds to the label and the other (monomer 2) binds to the molecule used to create a nanoenvironment.
Figure 14:
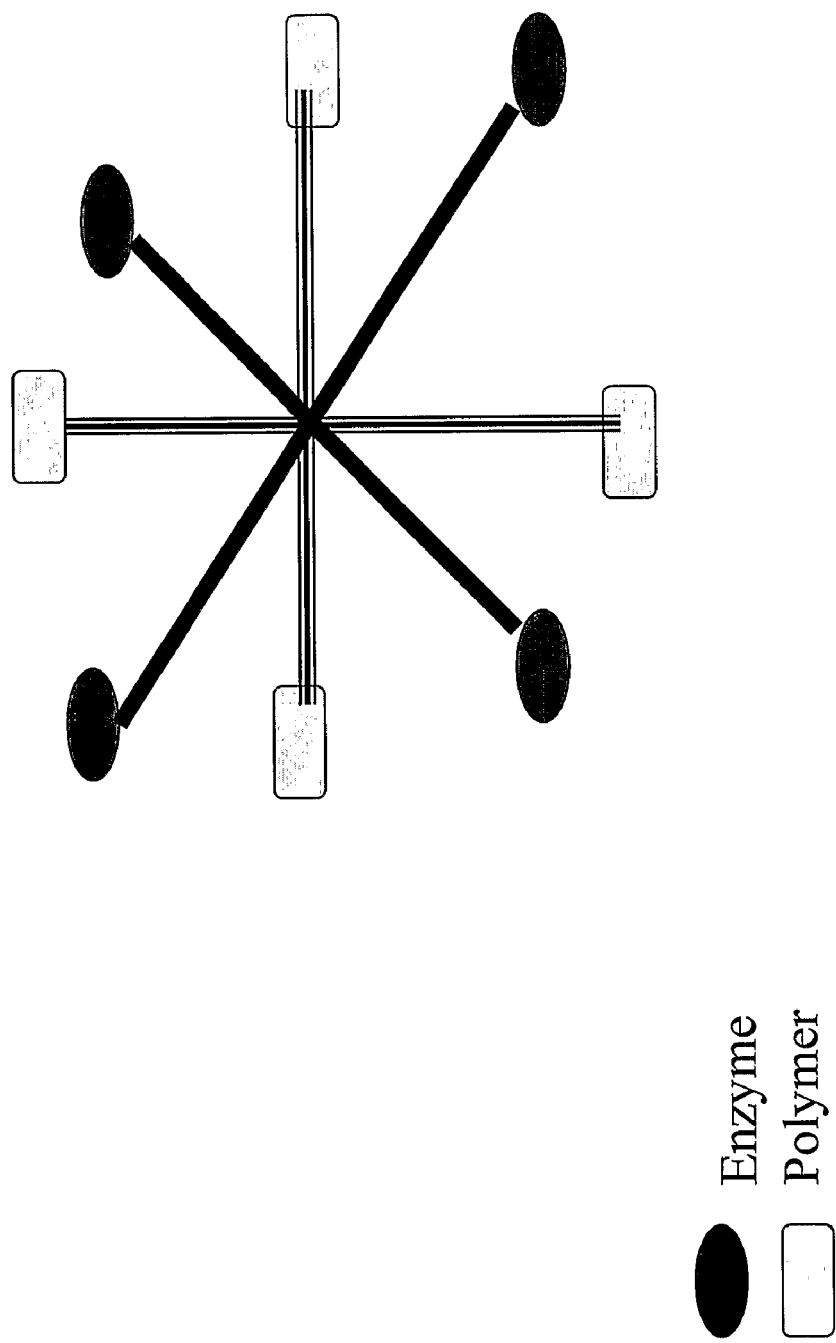
FIG. 14 provides an exemplary dendrimer as an example of a repetitive structure built-up from a set of monomers (e.g., DNA probes). The monomers can be chosen to provide attachment points for the label and for the molecule used to create a nanoenvironment. These 3D structures can have labels and molecule used to create a nanoenvironment on adjacent arms of the structure. The attached groups can have an ordered arrangement. The pictured structure is a branched molecule with enzyme and polymer groups attached. Alternatively, the structure of the dendrimer itself can be the enhancing polymer with enzyme conjugated at specified locations.
Figure 15:
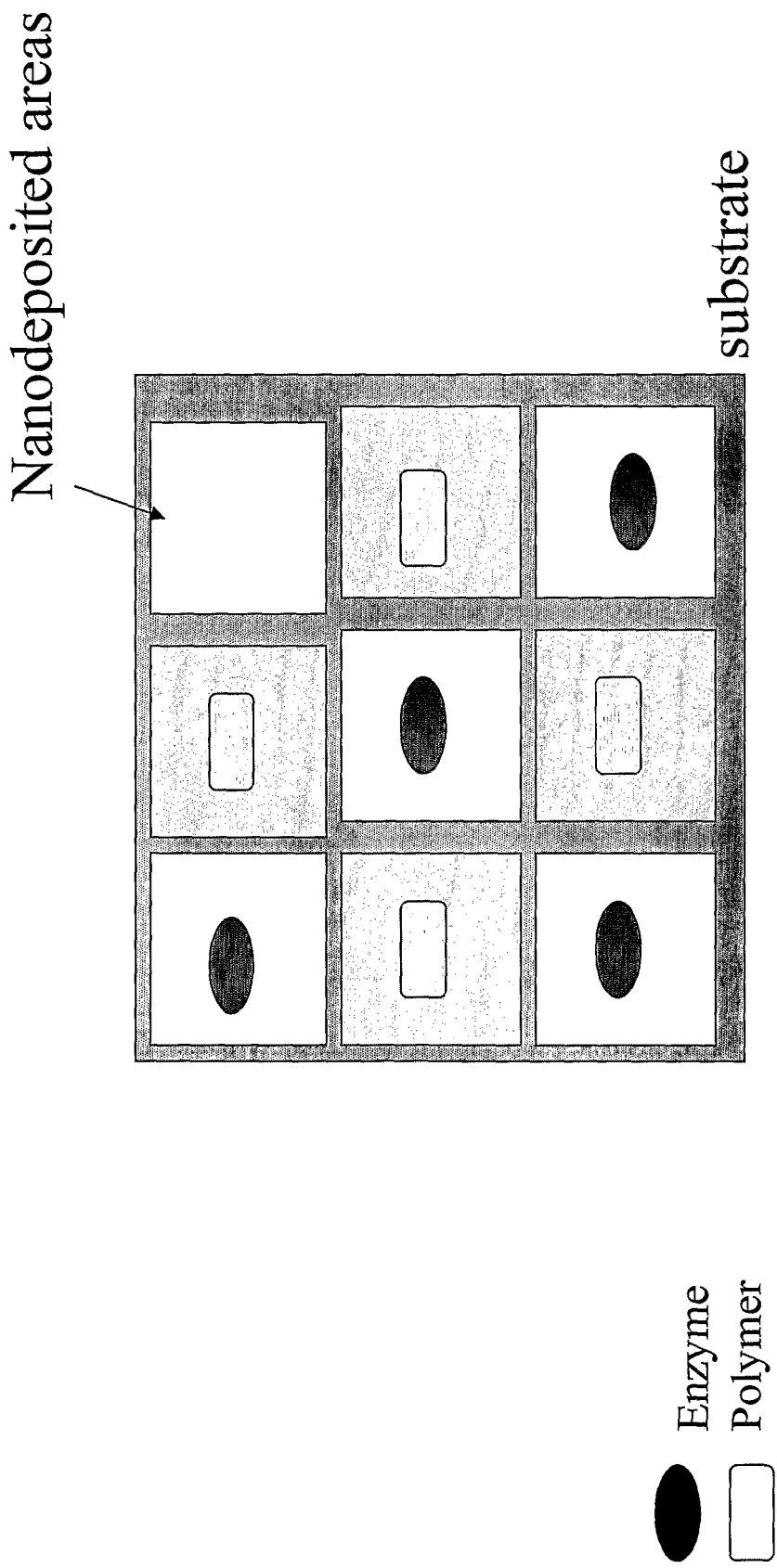
FIG. 15 provides an exemplary arrangement of nanometer dimensioned particles on a surface. Thus, rather than depositing a single molecule thick film with controlled orientation of enzyme and enhancer, blocks or particles of enzyme are directly conjugated to blocks or particles of enhancer.
Figure 16:
FIG. 16 provides an image of nylon tubes/rods in the aluminum oxide membrane. The arrow is pointing to a cavity indicative of a tubular structure.
Figure 17:
FIG. 17 provides an image of nylon tubes/rods with the aluminum oxide membrane removed FIG. 18 provides an image of nylon tubes/rods with the aluminum oxide membrane removed. The arrow is pointing to the matted solid surface that forms the base of the nanotube array. This base was in contact with the heated glass during fabrication.
Figure 18:
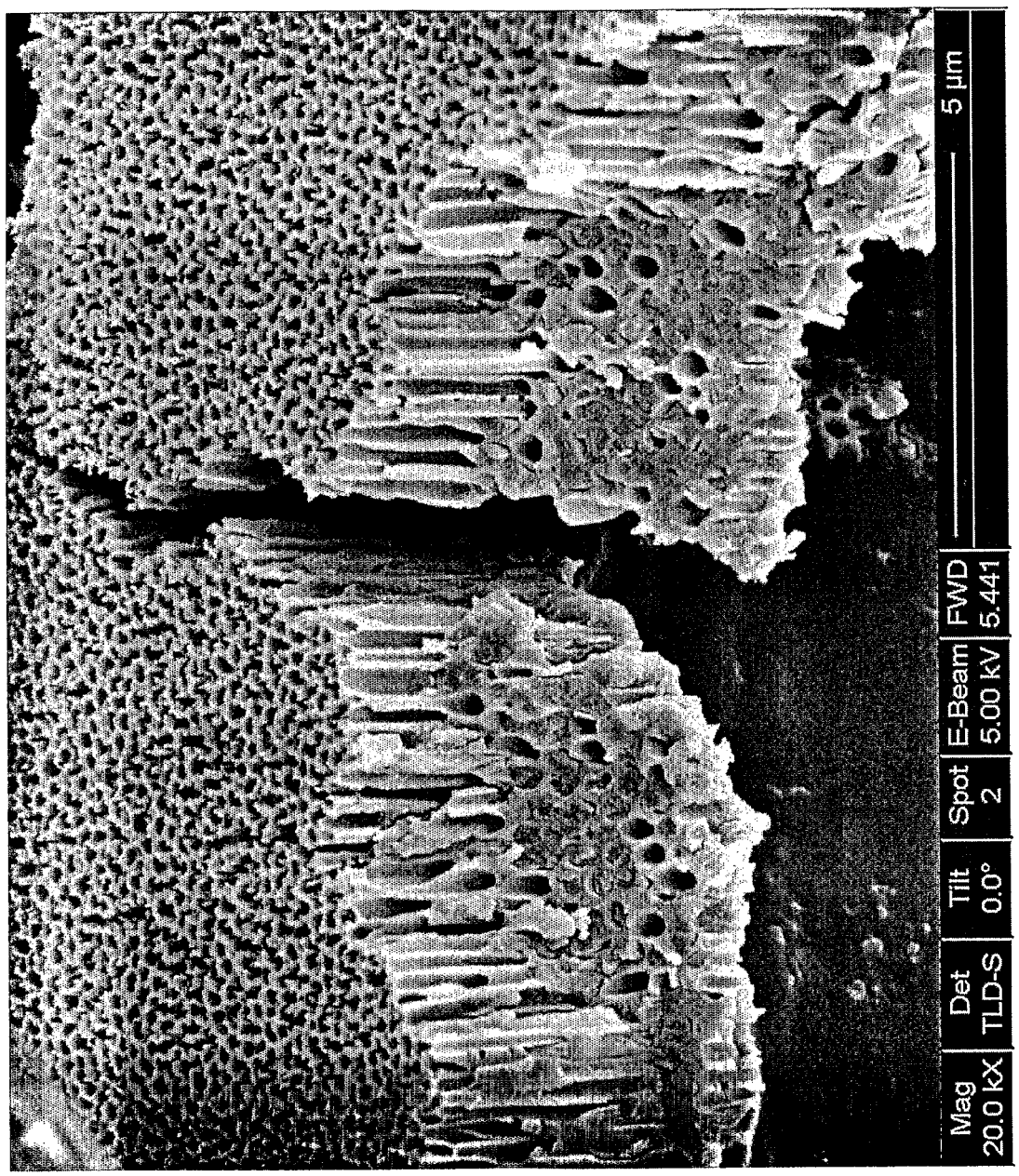
Figure 19:
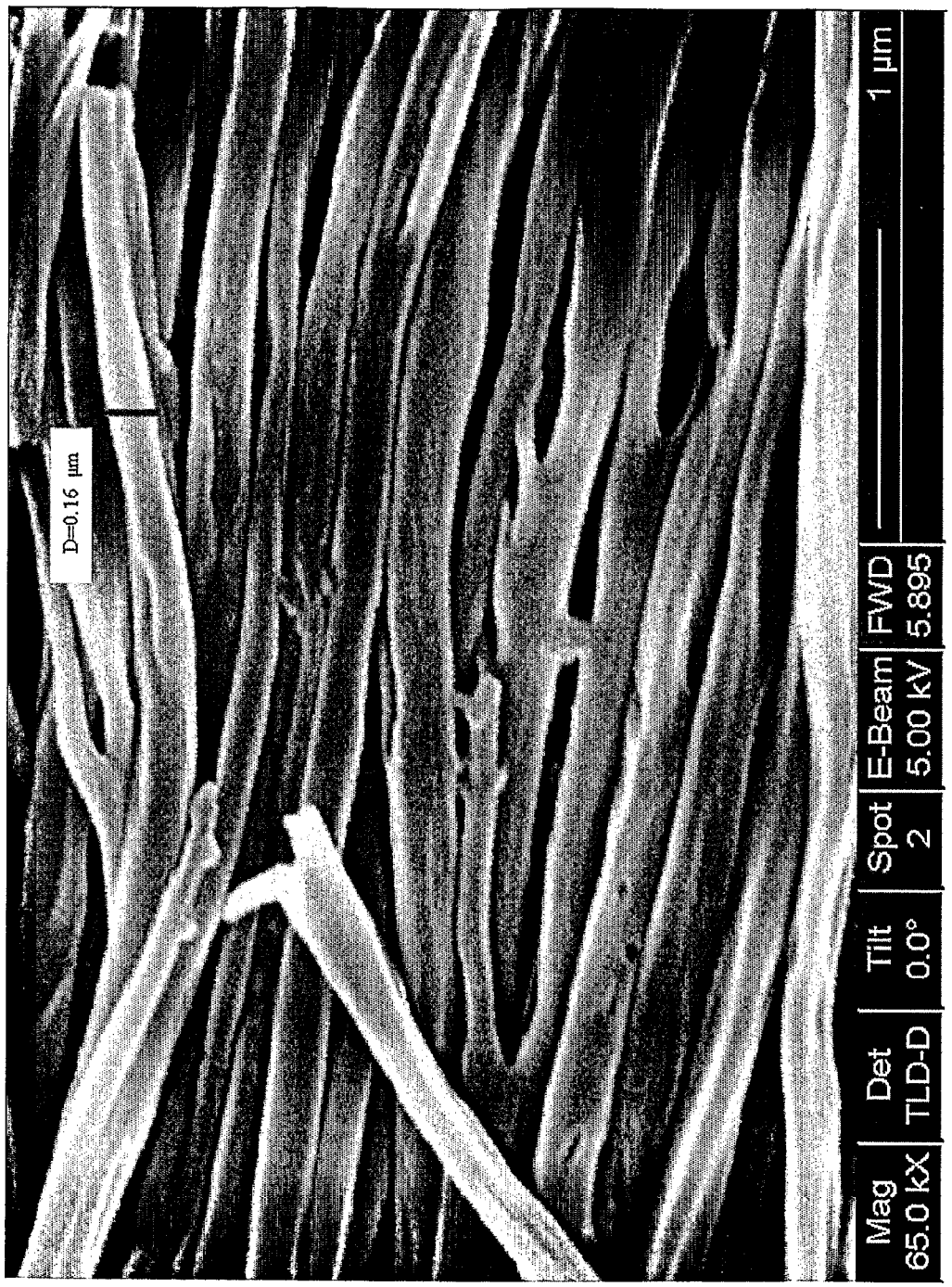
FIG. 19 provides an image of nylon tubes/rods with the aluminum oxide membrane removed. The segment is showing a width of the tubes as 160 nanometers.

This invention provides, inter alia, nanostructures associated with one or more luminescent labels for use in luminescent reactions. The nanostructures are preferably polymer loaded or fabricated from polymer.

Luminescence refers to the emission of light associated with the dissipation of energy from an electronic excited state of a substance. The term luminescent label as used herein refers to a protein, chemical, or other compound capable of directly or indirectly generating light (including fluorescent light) and thus a detectable signal. For example, in some embodiments, the label itself will emit light after excitation by an external source. In other embodiments, the label will react with a substrate or other compound which will then emit light.

A wide variety of fluorophores can be employed either alone, or in conjunction with quencher molecules, as the luminescent labels of the present invention. Chemiluminescent or bioluminescent labels can be also be employed herein. Luminescent labels of the present invention include, but are not limited to, enzymes, chemicals, catalytic antibodies, small molecule fluorophores, naturally occurring fluorescent proteins, engineered analogues of naturally occurring fluorescent proteins, metal complexes, and hemin.

The present invention provides a modified nanoenvironment to enhance the signal generated by luminescent labels. The components of the nanoenvironment include a scaffold comprising molecules, organic or inorganic, arranged in a nanostructural configuration; immobilized polymers; linked binding moieties; and a luminescent label.

For use herein, the term nanoenvironment refers to a local environment in the vicinity of a nanostructure.

Exemplary luminescent labels of the present invention include, for example, hydrolases (e.g., phosphatases such as alkaline phosphatase); esterases; glycosidases; oxidases (e.g., peroxidases such as horseradish peroxidase and microperoxidase); luciferases (e.g., firefly luciferase), aequorin; dioxetanes, dihydrophthalazinediones, metal complexes (e.g., lanthanide and actinide complexes); hemin; 1-and 2-aminonaphthalene; p,p'-diaminostilbenes, pyrenes; quaternary phenanthridine salts; 9-aminoacridines; p,p'-diaminobenzophenone imines; anthracenes; oxacarbocyanine; marocyanine; 3-aminoequilenin; perylene; bisbenzoxazole; bis-p-oxazolyl benzene; 1,2-benzophenazin; retinol; bis-3-aminopyridinium salts; hellebrigenin; tetracycline; sterophenol; benzimidzaolylphenylamine; 2-oxo-3-chromen; indole; xanthen; 7-hydroxycoumarin; phenoxazine; salicylate; strophanthidin; porphyrins; triarylmethanes; flavin; dansyl chloride; fluoresceins such as 3,6-dihydroxy-9-phenylxanthhydrol; rhodamineisothiocyanate; N-phenyl 1-amino-8-sulfonatonaphthalene; N-phenyl 2-amino-6-sulfonatonaphthalene: 4-acetamido4-isothiocyanato-stilbene-2,2'-disulfonic acid; pyrene-3-sulfonic acid; 2-toluidinonaphthalene-6-sulfonate; N-phenyl, N-methyl 2-aminoaphthalene-6-sulfonate; ethidium bromide; stebrine; auromine-0,2-(9'-anthroyl)palmitate; dansyl phosphatidylethanolamine; N,N'-dioctadecyl oxacarbocyanine; N,N'-dihexyl oxacarbocyanine; merocyanine, 4(3'pyrenyl)butyrate; d-3-aminodesoxy-equilenin; 12-(9'anthroyl)stearate; 2-methylanthracene; 9-vinylanthracene; 2,2'(vinylene-p-phenylene)bisbenzoxazole; p-bis[2-(4-methyl-5-phenyl-oxazolyl)]benzene; 6-dimethylamino-1,2-benzophenazin; retinol; bis(3'-aminopyridinium) 1,10-decandiyl diiodide; sulfonaphthylhydrazone of hellibrienin; chlorotetracycline;

N(7-dimethylamino-4-methyl-2-oxo-3-chromenyl)maleimide; N-[p-(2-benzimidazolyl)-phenyl]maleimide; N-(4-fluoranthyl)maleimide; bis(homovanillic acid); resazarin; 4-chloro-7-nitro-2,1,3benzooxadiazole; merocyanine 540; resorufin; rose bengal; and 2,4-diphenyl-3(2H)-furanone; green fluorescent proteins of cnidarians (Ward et al., Photochem. Photobiol. 1982; 35:803-808; Levine et al., Comp. Biochem. Physiol., 1982; 72B:77-85), yellow fluorescent protein from *Vibrio fischeri* strain (Baldwin et al., Biochemistry 1990; 29:5509-15), Peridinin-chlorophyll from the dinoflagellate *Symbiodinium* sp. (Morris et al., Plant Molecular Biology 1994; 24:673:77), phycobiliproteins from marine cyanobacteria, such as *Synechococcus*, e.g., phycoerythrin and phycocyanin (Wilbanks et al., J. Biol. Chem. 1993; 268: 1226-35).

Many such labels are commercially available from, for example, the SIGMA chemical company (Saint Louis, Mo.), Molecular Probes (Eugene, Oreg.), R&D systems (Minneapolis, Minn.), Pharmacia LKB Biotechnology (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersburg, Md.), Fluka Chemica-Biochemika Analytika (Fluka Chemie AG, Buchs, Switzerland), and Applied Biosystems (Foster City, Calif.), as well as many other commercial sources known to one of skill. Furthermore, those of skill in the art will recognize how to select an appropriate luminescent label for a particular application and, if it not readily available commercially, will be able to synthesize the necessary compound de novo or synthetically modify commercially available luminescent compounds to arrive at the desired label.

The luminescent labels of the present invention can be used with a wide range of energy donor and acceptor molecules to construct resonance energy transfer probes. Energy transfer can occur, for example, through fluorescence resonance energy transfer, bioluminescence energy transfer, or direct energy transfer. Fluorescence resonance energy transfer occurs when part of the energy of an excited donor is transferred to an acceptor fluorophore which re-emits light at another wavelength or, alternatively, to a quencher group that typically emits the energy as heat.

In a fluorescence energy transfer pair, it is generally preferred that an absorbance band of the acceptor substantially overlap a fluorescence emission band of the donor. When the donor (e.g., fluorophore) is a component of a probe that utilizes fluorescence resonance energy transfer, the donor moiety and the quencher (acceptor) of the invention are preferably selected so that the donor and acceptor moieties exhibit fluorescence resonance energy transfer when the donor moiety is excited. One factor to be considered in choosing the fluorophore-quencher pair is the efficiency of fluorescence resonance energy transfer between them. Preferably, the efficiency of energy transfer between the donor and acceptor moieties is at least 10%, more preferably at least 50% and even more preferably at least 80%.

There is a great deal of practical guidance available in the literature for selecting appropriate donor-acceptor pairs for particular probes, as exemplified by the following references: Pesce et al., Eds., Fluorescence Spectroscopy (Marcel Dekker, New York, 1971); White et al., Fluorescence Analysis: A Practical Approach (Marcel Dekker, New York, 1970); and the like. The literature also includes references providing exhaustive lists of fluorescent and chromogenic molecules and their relevant optical properties, for choosing reporter-quencher pairs (see, for example, Berlman, Handbook of Fluorescence Spectra of Aromatic Molecules, 2nd Edition (Academic Press, New York, 1971); Griffiths, Colour and Constitution of Organic Molecules (Academic Press, New York, 1976); Bishop, Ed., Indicators (Pergamon Press, Oxford, 1972); Haugland, Handbook of Fluorescent Probes and Research Chemicals (Molecular Probes, Eugene, 1992) Pringsheim, Fluorescence and Phosphorescence (Interscience Publishers, New York, 1949); and the like. Further, there is extensive guidance in the literature for derivatizing acceptor and quencher molecules for covalent attachment via readily available reactive groups that can be added to a molecule.

The term "nanostructure" as used herein refers to a scaffold comprising molecules, organic or inorganic, arranged in a nanostructural configuration. For use herein, a scaffold in nanostructural configuration is a structure that has at least one dimension that is about one micron or smaller. In preferred embodiments, the structure will have at least one dimension that is about 500 nm or smaller, preferably about 300 nm or smaller, and even more preferably 100 nm or smaller. The scaffold can be a hollow structure such as, for example, a fullerene (e.g., buckyball), single-walled nanotube, branched nanotube, kinked or bent nanotube, multi-walled nanotube, open or closed nanotube, nanowire, nanofiber, nanochannel or nanoparticle or any other surface or structure of nano-dimension. In addition to providing a location for the labels and polymer, the scaffold can also provide a physical constraint surrounding the label and polymer. The nanostructures can be freely mobile objects or the nanostructures can be fixed as an array of objects of a surface or be features that are part of a larger structure (e.g., a nanotubes or nanoposts fixed to a substrate to create an array).

For use herein, the terms nanotubes or nanotubules can be used interchangeably and refer to long thin hollow tubes that can have a single wall or multiple walls. The diameter of the tube is generally less than about 100 nm and the length is typically in the nanometer to centimeter range. Nanotubes have both outer and inner surfaces that can be differentially modified for chemical or biochemical functionalizations. Fullerene carbon nanotubes like regular carbon nanotubes are rolled up, highly ordered graphene sheets. Fullerene carbon nanotubes are, however, composed of more disordered forms of carbon. In addition to being described as long and thin, the nanotubes may be composed of a variety of shapes in profile as well as in cross-section. The shape can be diverse, including: tube, cone, oblong, cube, prism, pyramid, horn. The resulting profile or cross-section may be circular, rectangular, square, elliptical, hexagonal, pentagonal, trapezoidal, or other regular or irregular cross-sections.

The nanostructures can be constructed from a wide variety of materials, including, for example, carbon, silica, peptides, metals (e.g., palladium gold, lead zirconate titanate, and barium titanate), and organic polymers. Methods of constructing nanostructures are known in the art, for example, by pyrolytic or membrane deposition methods, by template synthesis, by wetting of porous templates or in-pore polymerization, by electroless deposition, or by sol-gel chemistry (Martin, Science 1994, 266, 1961-1966; Hulten et al. J. Mater. Chem. 1997, 7, 1075-1087; Cepak et al., J. Mater. Res. 1998, 13, 3070-3080; Nicewarner et al., Science 2001, 294, 137-141; Mitchell 2002;) and are thus not described herein in detail.

In some embodiments, the nanostructure will be fabricated from polymers. Nanostructures, such as nanotubes, can be fabricated from polymers using any method known in the art including self assembly or template-based fabrication. Self-assembly generally refers to the designed spontaneously association of structures or aggregates by noncovalent bonds (Whitesides et al, *Science* 1991; 254(5036):1312-9). An example of self-assembly mediated production of polymer nanotubes includes the use of amphiphilic block copolymers (Grumelard et al., *Chem Commun* 2004;13:1462-3). Alternatively, polymer nanotubes can be fabricated from cyclic peptide monomers (Ghadiri et al., *Nature* 1993;366:324-7). Template based fabrication generally refers to the molding of a polymer or the polymerization of monomers within a solid surface to produce tube or rod-like structures (Cepak et al, *Journal of Materials Research* 1998; 13: 3070-80.; Colquhoun H M et al., *J Mater Chem* 2003;13:1504-1506). Porous membranes can be used as templates for nanotube synthesis. Other templating methods include using nanorods that are coated with a polymer, e.g., polystyrene, and dissolution of a gold, glass, or silica wool nanorod to produce a hollow polymer nanotube.

In alternative embodiments, the nanostructure will be fabricated from polymer or a material other than polymers but will be polymer loaded. For use herein, a nanostructure that is polymer loaded is a nanostructure that has polymer associated with it. The polymer can be associated with the nanostructure using any means known in the art for directly or indirectly conjugating, linking, coupling or complexing molecules with each other. In some embodiments, the nanostructure will be polymer coated. The polymers are preferably immobilized on or in or around the nanostructure. Methods of immobilizing polymers on nanostructures are known in the art and can be by physical or chemical means, for example, by physical adsorption, covalent coupling, or layer-by-layer electrostatic techniques.

Carbon nanostructures are inherently hydrophobic (Chen et al., *J Am Chem Soc* 2001;123:3838-9) and this provides a means to physically immobilize other molecules onto the nanotube surface. For example, in one embodiment, the polymers will be adsorbed to carbon nanostructures simply by exposing suspensions of the nanostructures to the polymer. Alternatively, the polymer can be covalently coupled to the nanostructure, e.g., using an amino polyethylene glycol derivative. In some embodiments, carboxyl groups can be formed on the nanotubes (e.g., at the tip of a nanotube) thereby providing a site for conventional covalent attachment of biomolecules. As an alternative to forming carboxyl groups for attaching biomolecules, biomolecules can be directly embedded in the structure of the polymers. For example, a polymer solution can be mixed with a DNA strand that has biorecognition. Once the polymer solution is cast or coupled to a nanostructure, the DNA strand with biorecognition would also be part of the structure and can be available for sampling the environment.

Silica nanostructures are inherently hydrophilic. Means for attaching molecules to silica nanostructures include, for example, attaching hydrophobic octadecyl groups to the inside of template-synthesized silica nanotubes using octadecyl silane thereby providing a hydrophobic interior to the nanotube. Alternatively, silica nanostructures can be reacted with silanes, such as, for example, aminopropyltrimethoxysilane, and the amino group can provide an attachment point for the covalent immobilization of the polymers.

Any method can be used to associate polymers with the nanostructures to create exemplary polymer loaded nanostructures of the present invention. For example, the covalent grafting of organic or polymeric molecules on to carbon nanotubes has been accomplished by the "grafting-to" technique by using esterification and amidation reactions (Baskaran et al., *Agnew Chem. Int.* 2004; 43:2138-2142; Chen et al., *Science* 1998; 282:95-98; Sun et al., *Acc. Chem Res.* 2002;35: 1096-1104). Noncovalent functionalization methods have been used including polymer wrapping and "pi-pi" stacking on the surface of carbon nanotubes (Baskaran et al., *Agnew Chem. Int.* 2004;43:2138-2142). Polymer brushes on surfaces can be produced by the growth of polymer chains from covalently attached surface initiators using the "grafting from" strategy. Surface-initiated polymerization can be used to grow polymers on silicon, gold, carbon and clay nanostructures.

In one particular example, a sample of a multi-walled nanotube (MWNT) is refluxed with 50 mL of thionyl chloride and excess thionyl chloride is removed under vacuum. The activated nanotubes (MWNT-COCl) are washed with anhydrous THF and dried under vacuum. Hydroxyethyl-2-bromoisobutyrate in toluene is added to a flask that contains MWNT-COCl and the reaction is stirred at 100° C. for about 24 h under a pure $N_2$ atmosphere. After the reaction is finished, the solvent is completely removed under vacuum, the tubes are washed several times with ethanol and filtered. The initiator-attached tubes are dried at 40° C. for 10 hr under vacuum.

In an exemplary polymerization, hydroxyethyl-2-bromoisobutyrate treated nanotubes are placed in a clean glass ampoule attached with a septum adaptor connected to both nitrogen and a vacuum system. Styrene and a solution of CuBr and ligand in toluene are added into the ampoule with a syringe under $N_2$. The entire solution is degassed four times and sealed off under vacuum. The sealed ampoule is placed in an oil bath that is maintained at 100° C. and the reaction is stirred for 24 hr. After 24 h, the reaction is quenched by cooling with liquid $N_2$ and the ampoule is opened. The heterogeneous polymerization solution is diluted with THF and kept stirring in a round bottom flask for few hours to dissolve the soluble polymer. The supernatant THF is filtered and washed with THF. The polymer grafted nanotubes are recovered as lumpy aggregates and dried (Baskaran et al., *Agnew Chem. Int.* 2004;43:2138-2142).

In a polymer nanotube, the nanoenvironment can be created by the polymer that forms the sidewalls of the nanotube. Molecules introduced into the nanotube or adhered to the walls of the nanotube will experience the nanoenvironment created inside the nanotube or on the nanotube surface. Immobilization of polymers to the nanostructure can be random or localized. For example, in embodiments wherein the nanostructure is a nanotube, the polymer can be randomly immobilized on the inner and outer walls of the nanotube (Azamian et al., *J Am Chem Soc* 2002;124:12664-5; Chen et al., *J Am Chem Soc* 2001;123:3838-9; Erlanger et al., *Nano Letts* 2001;1:465-7; Shim et al., *Nano Letts* 2002;2:285-82; Wang et al., *J Am Chem Soc* 2004;126:3010-1). Alternatively, in embodiments wherein the nanostructure is a nanotube and the immobilization is selective or localized, the polymer can be localized to the tip (Wong et al., *Nature* 1998;394:52-55) or the inner (Lee et al., *Science* 2002;296:2198-200) or outer walls of the nanotube (Mitchell et al., *J Am Chem Soc* 2002; 124:11864-5) or even entrapped within a capped nanotube. Selective immobilization can be achieved, for example, by growing nanotubes in membrane pores (Martin, *Science* 1994;266:1961-6). The membrane can act as a mask for the outer surface and allow selective immobilization on the inner surface of the nanotube. Selective immobilization can also be achieved by entrapment. For example, a nanotube can act as a container for enzyme labels. Generally, the size of an enzyme (e.g., alkaline phosphatase 5.77 nm×6.99 nm×11.15 nm; peroxidase 15.89 nm×15.89 nm×11.43 nm; firefly luciferase 11.95 nm×11.95 nm×9.54 nm) would restrict this to relatively large diameter nanotubes. Entrapped enzyme can move freely within the confines of the nanotube and yet be subject to the nanoenvironment created by other molecules present either in solution constrained by the nanotube pores or immobilized on the nanotube surface. In some embodiments the nanotube will be capped. Any method of capping nanotubes can be used, for example, by growing nanotubes in pores and then occluding the open end of the nanotube with glue (Martin, *Science* 1994;266:1961-6).

The microenvironment provided by polymers and more ordered structures such as micelles has been shown to have a beneficial effect on many different types of chemical reaction (Martinek et al., *Eur J Biochem* 1986;155:453-68). Soluble polymers can also have pronounced effects on luminescent reactions. While not wishing to be bound by any particular theory, the polymer effect may be due to one or more of the following processes—sequestration of inhibitory products (Kricka and DeLuca, *Arch Biochem Biophys* 1982; 217: 674-80), stabilization of reaction intermediates by hydrophobic regions of the polymer, creation of an environment that limits collisional deactivation of electronically excited state intermediates by solvent, or facilitating energy transfer to fluorophore acceptors added to the reaction mixture.

The term "polymer", as used herein, refers to molecules formed from the chemical union of two or more repeating units. Accordingly, included within the term "polymer" may be, for example, dimers, trimers and oligomers. The polymer may be synthetic, naturally-occurring or semisynthetic. Any polymer can be used in the present invention. Preferably the polymer will provide a more hydrophobic environment. Polymers for use in the present invention can include for example, materials that can be converted into nanofibers, such as, for example, poly(lactic acid-co-glycolic acid), poly(acrylic acid)-poly(pyrene methanol), sodium citrate, polypyrrole, poly(3-methylthiophene), polyaniline, polyacrylonitrile, poly(p-phyenylene), poly(3,4-ethylenedioxythiophene), polyacrylonitrile, poly(L-lactic acid)-polycaprolactone, blends, polystyrene-block-poly(2-cinnamoylethyl methacrylate), polystyrene-block-poly(2-cinnamoylethyl methacrylate)-block-poly(tert-butyl acrylate), peptide-amphiphile, dendrimer, bolaform glucosamide; materials that can electrospun into nanofibers, such as for example, polystyrene, polycarbonate, polymethacrylate, polyvinylchloride, polyethylene terephthalate, nylon6,6, nylon4,6, polyamide, polyurethanes, polyvinyl alcohol, polylactic acid, polycaprolactone, polyethylene glycol, polylactide-co-glycolide, polyethylene-co-vinyl acetate, polyethylene co-vinyl alcohol, polyethylene oxide, collagen; amphiphilic poly(2-methyloxazoline-block-dimethylsiloxane-block-2-methyloxazoline) (PMOXA-b-PDMS-b-PMOXA) ABA triblock copolymers; poly(thiophene); polyetherketone; polyallylamine; polyethyleneimine; poly(iminohexamethylene); polytetrafluoroethylene; poly(oxy-1,4,-phenyleneoxyl-1,4-phneylenecarbonyl-1,4-phenylene); polyvinylidene fluoride; polymethyl methacrylate; polystyrene; aluminum; palladium; silicon; or blends or composites thereof.

For use in the present invention, a luminescent label is preferably associated with a polymer loaded nanostructure or a polymer fabricated nanostructure or combination thereof. For use herein, a luminescent label can be associated with the nanostructure using any means known in the art for directly or indirectly conjugating, linking, coupling, or complexing molecules with each other, for example, by physical, chemical or other means of attraction. In some embodiments, the label will be associated with the nanostructure before attachment or immobilization of a polymer to the nanostructure. In exemplary embodiments, the labels can be conjugated to the nanostructures or polymer loaded nanostructures by physical or chemical means, for example, by physical adsorption or covalent coupling. In preferred embodiments, multiple copies of the label will be conjugated to the polymer loaded nanostructure. Particularly preferred labels of the present invention include catalytic molecules such as phosphatase enzymes (e.g., alkaline phosphatase), peroxidase enzymes (e.g., horseradish peroxidase), and luciferase enzymes (e.g., firefly luciferase).

Methods of conjugating functional groups to nanostructures are known in the art and can be by physical or chemical means, for example, by physical adsorption, non-covalent or covalent coupling. For example, attachment of biomolecules onto and into carbon nanotubes can be accomplished by non-covalently attaching a reactive molecule to the sidewalls of the nanotubes. The reactive molecule can then be used to attach the biomolecules to a wall of the nanotube.

In one particular example, protein adsorption is carried out by immersing nanotubes in a phosphate buffer solution (pH 7) at a protein concentration of approximately 0.7 microgram/mL for 1 h followed by thorough water rinsing (Shim et al., *Nano Letts* 2002;2:285-8). To a dispersion of oxidized nanotubes in pure water is added a dilute solution of protein. The suspension is left to stand and then tubes are washed thoroughly on a 0.4 micrometer polycarbonate membrane with HPLC-grade water. (Bobak et al., *J. Am. Chem. Soc.* 2002; 124:12664-12665).

In one particular example, alkaline phosphatase is covalently coupled to carbon nanotubes by physical adsorption. (Wang et al., *J Am Chem Soc* 2004;126:3010-1). A 0.2% Triton-X suspension containing 0.5 mg oxidized nanotubes, 100 mM MES, 100 mM NHS, and 100 mM EDAC (set to pH 6.0 with 0.1 M HCl) is sonicated for 1 h at room temperature. Following the activation, the pH is adjusted to 8.5, and the amino-modified oligonucleotides and alkaline phosphatase is added. The reaction mixture is stirred overnight at room temperature. Following this incubation, the mixture is washed with deionized water and 0.5M NaCl during several centrifugation cycles at 14000 rpm. Subsequently, the samples are allowed to stand at room temperature for few hours, and the supernatant fractions are collected.

The nanostructures of the present invention have binding specificity for an analyte of interest, i.e., the nanostructures are capable of specifically binding directly or indirectly to an analyte of interest. The binding specificity can be inherent to the nanostructure (Zheng et al., *Science* 2003; 302: 1545-1548; Wang et al., *Nature Materials* 2003 2: 196-200) or can be imparted to the nanostructure by a binding moiety. The term "analyte" refers to the substance to be detected that may be present in the sample. The analyte can be any substance for which there exists a naturally occurring specific binding member (such as an antibody or antigen), or for which a specific binding member can be prepared. The analyte, or portion thereof, can be antigenic or haptenic having at least one determinant site, or can be a member of a naturally-occurring binding pair, e.g., carbohydrate and lectin, hormone and receptor, complementary nucleic acids (e.g., DNA, RNA, mRNA) and the like. Analytes of particular interest include DNA, RNA, antigens, antibodies, proteins, peptides, carbohydrates, polysaccharide, glycoprotein, haptens, drugs, hormones, hormone metabolites, macromolecules, toxins, bacteria, viruses, enzymes, tumor markers, nucleic acids, and the like, although other types of substances can also be detected.

The phrase "specifically binds to" or "having binding specificity" when referring to a binding reaction, refers to a binding reaction which is determinative of the presence of a target analyte in the presence of a heterogeneous population of proteins and other biologics. A nanostructure having binding specificity for an analyte of interest is capable of binding directly or indirectly to the analyte with a high affinity. In an exemplary embodiment, binding can be by covalent bonding, ionic bonding, ion pairing, electrostatic interaction, van der Waals association and the like. In embodiments, wherein a binding moiety imparts the binding specificity, the binding moiety can be a specific binding substance capable of binding directly or indirectly to the analyte with a high affinity. The binding moiety is preferably substantially free from cross-reactivity with other substances that may be present in the sample or the assay reagents. The binding moiety can be a detector probe such as an oligonucleotide, peptide, ligand, antibody, antigen, or other small molecule that directly binds the analyte of interest.

While the binding moiety in some embodiments will bind directly to the analyte, the present invention contemplates indirect binding of the binding moiety to the analyte, i.e., the use of one or more intermediate binding substances to sequester or effect a linkage to the analyte. For example, in some embodiments, the binding moiety will bind to its binding partner which is itself bound to a detector probe bound to the analyte of interest. For example, in embodiments wherein the analyte is RNA or DNA, the binding moiety can be a binding agent such as streptavidin bound to a biotinylated oligonucleotide complementary to the RNA or DNA sequence of interest. When binding to a solid phase, for example, it will be possible to provide, on the solid phase, a detector probe bound to the analyte of interest and linked to an intermediate binding substance which is able to bind directly to the binding moiety linked to a nanostructure of the present invention. A wide variety of indirect binding protocols are available and well described in the scientific and patent literature. The term "binding moiety" as used in the specification and claims are thus intended to include all substances which are able to bind the analyte, either directly (i.e., without an intermediate binding substance) or indirectly (i.e., with one or more intermediate binding substances forming a linkage).

The nanostructures can be linked to a component of a binding reaction, e.g., a binding moiety, in order to be used in an immunoassay or DNA probe assay although they need not be. Alternatively, the binding moiety may be directly embedded into the nanostructure. In an exemplary embodiment, the nanostructures will be linked to biotiti or streptavidin because the resultant streptavidinylated nanostructures and biotinylated nanostructures are universal conjugates that can be used in any immunoassay or DNA probe assay. The binding moiety can be conjugated to the nanostructures by physical or chemical means, for example, by physical adsorption or covalent coupling. For example, in one embodiment, biotin can be attached to carbon nanotubes by first adsorbing diamino-PEG to the nanotubes during an incubation period. The adsorbed diamino-PEG on the nanotubes can then be exposed to biotinamidocaproic acid 3-sulfo-N-hydroxysuccininimide ester in phosphate buffer for about 3 hours. Alternatively, biotin can be attached to carbon nanotubes by first exposing the nanotubes to 1-pyrenebutanoic acid succinimidyl ester for about 1 hour at room temperature. After rinsing and washing with DMF and methanol the coupling reagent adsorbed to the nanotube surface will be reacted with biotin-PEO-amine for about 18 hours at room temperature (Chen et al., *J Am Chem Soc* 2001;123:3838-9). In another embodiment, biotin can be attached to carbon nanotubes by first exposing the nanotubes to a mixture of 5-(biotinyamido)pentylamine and EDC in MES buffer at room temperature for about 2 hours. In yet another embodiment, biotin can be attached to carbon nanotubes by covalently coupling an amino-biotin derivative (e.g., 5-(biotinyamido)pentylamine or biotin-PEO-amine) to carboxyl groups on the carbon nanotube surface using 1-ethyl-3-(3-dimethyl aminopropyl)carbodiimide (Wang et al., *J Am Chem Soc* 2004;126:3010-1). A suspension of the nanotubes will be treated with EDAC and NHS for about 1 hour at room temperature and then the activated nanotubes exposed to the biotin derivative at a pH of about 8.5. Methods of conjugated streptavidin to the nanotubes are known in the art. Adsorption can be achieved, for example, by mixing together a solution of streptavidin in 10 mM phosphate buffer with the carbon nanotubes for about 1 hour at room temperature (Shim et al., *Nano Letts* 2002;2:285-8).

The presence of biotin groups or streptavidin groups on the nanotubes can be demonstrated by binding of fluorescein-avidin or fluorescein-streptavidin. Fluorescence associated with the nanotube fraction will provide a measure of the biotinylation or streptavidinylation.

In certain embodiments, the polymers to be used in the present invention are assembled by layer-by-layer technique on a scaffold consisting of a nanotube, nanowire or any alternative nanostructural configuration. The "layer-by-layer" technique is generally a sequential self-assembly of layers of differing compositions onto a solid scaffold. The scaffold can provide a point of attachment of multiple enzymatic and chemical labels and detector probes such as oligonucleotides, peptides, ligands, and antibodies. Additional molecules can also be attached to the scaffold to provide other functionalities.

Layer-by-layer assemblies are, in general, believed to be stabilized by electrostatic interactions between each of the layers. In certain aspects of the present invention, the layer-by-layer assemblies can be stabilized against desorption by capping the final layered structure with a layer of polyelectrolyte, resulting in some electrode films that are stable in air at room temperature for weeks (Lvov, et al., *J. Am. Chem. Soc.* 1998, 120, 4073-80 and Pastorino, et al., *Biotechnology and Bioengineering* 2003, 84, 286-91).

In certain embodiments, the technique of layer-by-layer assembly is applied to carbon nanotubes to create nanostructures for use in the present methods. Assemblies of polyelectrolytes can be layered with bulk sheets of carbon nanotubes (Mamedov, et al, *Nature Materials* 2002, 1, 190-4 and Rouse & Lillehei, *Nano Letters* 2003, 3, 59-62). In addition, layer-by-layer assembly of polyelectrolytes can be applied to individual carbon nanotubes to increase solubility and facilitate noncovalent modification. Similar to the assembly of electrode films, individual carbon nanotube templates can be used to build structures with electrostatically assembled layers. An example of an assembly is as follows. In a first step, a strong charge is formed around the nanotubes by carboxylation. In a second step, absorption of alternating polycation and polyanion layers of polyelectrolytes occurs.

Exemplary polyelectrolytes that can be used in electrostatic layer-by-layer assemblies include cationic polymers such as: PDDA—poly(diallyldimethyl ammonium chloride), PAH—poly(allylamine hydrochloride), PEI—poly(ethyleneimine), PLL—poly(lysine), and chitosan; as well as anionic moieties such as PSS—poly(styrenesulfonate), poly (sodium 4-styrenesulfonate), PAPSA—poly(anilinepropanesulphonic acid), PVS—poly(vinylsulphonate), PAA—poly (acrylic acid), heparin, and DNA. Preferably, the polyelectrolytes will be ones that enhance the luminescent enzyme catalyzed reactions not only by providing for more luminescent label to be conjugated to the nanostructure but by modulating, e.g., enhancing, the luminescent signal created by the luminescent enzyme catalyzed reactions. Other polymers described herein can also be used in the layer-to-layer technique as long as there is electrostatic attraction between the polymer layers.

Luminescent label, such as enzymes for use in chemilumenscent assays, can be added into the layer-by-layer assembly. For example, carboxylated nanotubes can be absorbed with alternating layers of polymer and enzyme and the structure can be capped with an outermost layer of polymer. This enzyme packed carbon nanotube can then, in certain embodiments, be modified with a binding moiety, such as, for example, streptavidin to then be attached to any number of nucleic acid or protein ligands. This layer-by-layer approach can provide an increase in detection by allowing for a high degree of enzyme loading. For example, the increase in monolayer deposition of an enzyme, such as alkaline phosphatase, to a single walled carbon nanotube is estimated to be approximately five-fold higher by electrostatic assembly (layer-by-layer) compared to covalent attachment.

The layered structures can be assembled on any scaffold such as a single-walled nanotube, branched nanotube, kinked or bent nanotube, multi-walled nanotube, open or closed nanotube, nanowire, nanofiber, nanochannel, nanoparticle or any other surface or structure of nano-dimension. This scaffold creates a location for multiple label molecules.

Binding moieties including detector probes such as oligonucleotides, peptides, ligands, antibodies and small molecules can be conjugated to the scaffold by direct absorption or by specific conjugation reactions as described herein.

As well as providing nanostructures associated with luminescent label, the present invention provides methods of using such nanostructures to determine the presence or concentration of an analyte in a sample. The methods can comprise the steps of providing to the sample a nanostructure having binding specificity to an analyte; generating luminescence; and measuring the amount of luminescence generated. In some embodiments, methods of determining the presence of an analyte in sample will comprise the step of providing to the sample a nanostructure having binding specificity to an analyte and detecting the presence or absence of luminescence wherein the presence of luminescence indicates that the analyte is present in the sample. In some embodiments, it will be necessary to remove unbound nanostructure from the sample before generating the luminescence. In other embodiments, for example, embodiments wherein the assay for determining the presence or concentration of analyte is a non-separation assay, a washing step will be undesirable.

The present invention also provides methods for detecting an analyte in a sample. In an exemplary embodiment, the methods comprise the steps of contacting the sample with a nanostructure having binding specificity for the analyte, wherein said nanostructure is associated with a first luminescent label; contacting the sample with a second luminescent label that emits light at a different wavelength than said first luminescent label, said second luminescent label having binding specificity for said analyte; generating luminescence by exciting said first luminescent label; and detecting the presence or absence of luminescence from said second luminescent label; wherein the presence of luminescence from said second analyte indicates that the analyte is present in the sample. The binding specificity for the second analyte may be imparted to the second luminescent label by association with a binding moiety specific for the analyte and/or by association with a nanostructure specific for the analyte.

The present invention also provides methods for detecting whether a first analyte is in close proximity to a second analyte in a sample. The methods can comprise the steps of contacting the sample with a nanostructure associated with a first luminescent label and having binding specificity for said first analyte; contacting the sample with a second luminescent label that emits light at a different wavelength than said first luminescent label, said second luminescent label having binding specificity for said second analyte; generating luminescence by exciting said first luminescent label; and detecting the presence or absence of luminescence from said second luminescent label; wherein the presence of luminescence indicates that the first analyte is in close proximity to the second analyte. The binding specificity for the second analyte may be imparted to the second luminescent label by association with a binding moiety specific for the analyte and/or by association with a nanostructure specific for the analyte.

The present invention also provides methods for detecting an analyte in a sample, comprising the steps of providing a nanostructure; sequentially applying a plurality of layers to said nanostructure, said layers comprising a chemiluminescent enzyme, a fluorescent molecule or a combination thereof, to produce a nanostructure having luminescent label associated with it; the nanostructure having binding specificity for the analyte; contacting a sample with the nanostructure; optionally removing any unbound nanostructure from the sample; causing any label present in the sample to generate luminescence; and detecting the presence or absence of luminescence wherein the presence of luminescence indicates that the analyte is present in the sample. The binding specificity for the second analyte may be imparted to the second luminescent label by association with a binding moiety specific for the analyte and/or by association with a nanostructure specific for the analyte.

The methods can further comprise the steps of providing to the sample a labeled detector probe capable of specifically binding to the analyte. In such embodiments, the binding moiety will be capable of specifically binding to the labeled detector probe. The labeled detector probe can be any type of molecule capable of specifically binding to the analyte of interest, including, for example, oligonucleotide, peptide, ligand, antibody, antigen, or other small molecule that directly binds the analyte of interest. For example in embodiments, wherein the analyte is nucleic acid, the detector probe can comprise a nucleic acid sequence complementary to the analyte.

The term "complementary," as used herein, refers to the capacity for precise pairing of two nucleobases regardless of where the two are located. For example, if a nucleobase at a certain position of an oligomeric compound is capable of hydrogen bonding with a nucleobase at a certain position of a target nucleic acid, then the position of hydrogen bonding between the oligonucleotide and the target nucleic acid is considered to be a complementary position. The oligomeric compound and the target nucleic acid are complementary to each other when a sufficient number of complementary positions in each molecule are occupied by nucleobases that can hydrogen bond with each other. Thus, "complementary" indicates a sufficient degree of precise pairing or complementarity over a sufficient number of nucleobases such that stable and specific binding occurs between the oligonucleotide and a target nucleic acid. It is understood in the art that the sequence of the oligomeric compound need not be 100% complementary to that of its target nucleic acid to be specifically hybridizable or to specifically bind.

In some embodiments, the luminescent label will be of the kind that interacts with a substrate or other bio-or chemi-luminescent reactant to generate luminescence. The bio-or chemi-luminescent reactant can be any substance which causes or undergoes a chemical or biological reaction leading to the emission of light. A wide variety of substrates (e.g., luminescent compounds) have been identified in the art for use with luminescent assays. These include, but are not limited to, 1,2-dioxetanes, cyclic diacylhydrazide compounds, and luciferin for use with enzymes such as phosphatases (e.g., alkaline phosphatase), peroxidases (e.g., horseradish peroxidase) and luciferases (e.g., firefly luciferase).

Dioxetanes are compounds having a 4-membered ring in which 2 of the members are oxygen atoms bonded to each other. Dioxetanes can be thermally or photochemically decomposed to form carbonyl products, e.g., ketones or aldehydes. Release of energy in the form of light (i.e. luminescence) accompanies the decompositions. The dioxetanes can be used in an assay method in which a member of a specific binding pair (i.e. two substance that bind specifically to each other) is detected by means of an optically detectable reaction. According to this method, the dioxetane is contacted with an enzyme that causes the dioxetane to decompose to form a luminescent substance (i.e. a substance that emits energy in the form of light). The luminescent substance is detected as an indication of the presence of the first substance. By measuring, for example, the intensity of luminescence or the total amount of luminescence, the concentration of the first substance can be determined. Where the enzyme is an oxido-reductase (preferably a peroxidase, e.g., horseradish peroxidase or rnicroperoxidase), it causes the dioxetane to decompose by cleaving the O—O bond of the 4-membered ring portion of the dioxetane. The enzyme can act directly on the dioxetane substrate or can be mediated through the addition of peroxide. Where the dioxetane includes an enzyme cleavable group (e.g., phosphate), the enzyme (e.g., phosphatase) causes the dioxetane to decompose by cleaving the enzyme cleavable group from the dioxetane. Cleavage yields a negatively charged atom (e.g., an oxygen atom) bonded to the dioxetane, which in turn destabilizes the dioxetane, causing it to decompose and emit radiation, which in turn is absorbed by the portion of the molecule containing the fluorescent chromophore, which consequently luminesces.

1,2-dioxetanes are well established in the art. Suitable dioxetanes are for example those disclosed in U.S. Pat. Nos. 4,978,614; 4,952,707; 5,089,630; 5,112,960; 5,538,847; 4,857,652; 5,849,495; 5,547,836; 5,145,772; 6,287,767; 6,132,956; 6,410,751; 6,353,129; 6,284,899; 6,245,928; 6,180,833; 5,892,064; 5,886,238; 5,866,045; 5,578,523; each of which is incorporated by reference herein in its entirety and for all purposes. In some embodiments, a hydrophobic fluorometric substrate is used in conjunction with the 1,2-dioxetane. A hydrophobic fluorometric substrate is a compound which upon activation by an enzyme can be induced to emit in response to energy transfer from an excited state dioxetane decomposition product donor. As the donor is hydrophobic, the substrate, when activated, must be sufficiently hydrophobic as to be sequestered in the same hydrophobic regions to which the donor migrates, for energy and transfer to occur. Exemplary fluorometric substrates are AttoPhos™ and AttoPhos Plus™ invented by JBL Scientific Inc. and distributed by Promega.

In general, any chemiluminescent dioxetane which can be caused to decompose and chemiluminesce by interaction with an enzyme can be used in connection with this invention. Suitable dioxetanes are available from commercial sources such as the AMPPD™, CSPD™, CDP™, and CDP™-Star substrates marketed by Tropix (Bedford, Mass.) and Lumigen PPD™, Lumi-Phos™, Lumi-Phos 530™, and Lumi-Phos Plus™, available from Lumigen Inc. (Southfield, Mich.).

Typically, the 1,2-dioxetanes useful in this invention will have the general formula:

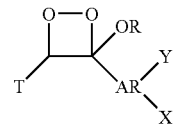

In these 1,2-dioxetanes, T is a stabilizing group. Because the dioxetane molecule, without the stabilizing group, may spontaneously decompose, a group, typically a polycycloalkyl group is bound to the dioxetane to stabilize it against spontaneous decomposition. This need for stabilization has resulted in commercially developed 1,2-dioxetanes being generally spiroadamantyl. The adamantyl group, spirobound, can be optionally substituted at any bridge head carbon, to affect chemiluminescent properties. As indicated, the remaining carbon of the dioxetane ring bears a OR substituent, wherein R is generally an alkyl or cycloalkyl, although it may be a further aryl group. The alkyl can be optionally substituted, with the substituent including halogenated groups, such as polyhaloalkyl substituents. The remaining valence is occupied by an aryl moiety, preferably phenyl or naphthyl. If naphthyl, particular substitution profiles on the naphthyl ring are preferred. The aryl ring bears at least one substituent, X. In commercially developed dioxetanes, this is typically an enzyme-cleavable group. Where the associated enzyme is alkaline phosphatase, for example, the enzyme-cleavable group X will be a phosphate. The aryl ring may also bear a substituent Y, which is selected to be either electron donating, or electron withdrawing. Preferred groups include chlorine, alkoxy and heteroaryl, although other groups may be employed. These substitutions can further effect chemiluminescent properties, and reaction kinetics. A wide variety of other substituents are disclosed in the referenced patents.

A class of compounds receiving particular attention with respect to luminescent reactions utilizing a peroxidase enzyme, e.g., horseradish peroxidase, are dihydrophthalazinedione compounds that are used in combination with an oxidant, preferably a peroxide compound such as hydrogen peroxide. Any chemiluminescent dihydrophthalazinedione can be used as substrate in the present invention, that is to say any dihydrophthalazinedione which is oxidisable in the presence of a peroxidase catalyst by an addition of an oxidant to give chemiluminescence. Dihydrophthalazinediones are well established in the art. Suitable dihydrophthalazinediones as well as other compounds for use with peroxidases, (e.g., acridinium compounds, such as acridinium esters and benzacridinium, and alkenes) are, for example, those disclosed in U.S. Pat. Nos. 5,552,298; 6,696,569; 6,410,732; 5,922,558; 5,750,698; 5,723,295; 5,670,644; 5,601,977; 5,552,298; 5523212; 5,879,894; 6,635,437; 6,296,787; 6,270,695; 6,218,137; 6,139,782; 6,126,870; 6,045,991; 5,965,736; 5,840,963; 5,772,926; and 5,686,258; each of which is incorporated herein by reference in its entirety. Preferred dihydrophthalazinediones include substituted aryl cyclic diacylhydrazide including aminoaryl cyclic diacylhydrazides such as luminol, isoluminol, aminobutylethylisoluminol, aminoethyl-ethylisoluminol and 7-dimethylaminonaphthalene-1,2-dicarboxylic acid hydrazide and hydroxyaryl cyclic diacylhydrazides, for example, 5-hydroxy-2,3-dihydro-phthalazine-1,4-dione; 6-hydroxy-2,3-dihydro-phthalazine-1,4-dione; 5-hydroxy-2,3-dihydro-benzo[g]phthalazine-1,4-dione; and 9-hydroxy-2,3-dihydro-benzo[f]phthalazine-1,4- dione. Peroxide compounds include hydrogen peroxide, sodium perborate, urea peroxide, and the like.

The sensitivity of the peroxidase-catalyzed chemiluminescent oxidation of dihydrophthalazinediones can be enhanced by including an enhancer in the reaction. The enhancer will be present in an amount which enhances light production from the diacylhydrazide in the presence of the peroxidase and/or decreases background chemiluminescence. Enhancers are known in the art and include, phenolic compounds such as those disclosed in U.S. Pat. No. 5,306,621, incorporated herein by reference in its entirety, including p-phenylphenol, p-iodophenol, p-bromophenol, p-hydroxycinnamic acid 6-bromo-2-naphthol, D-luciferin, and 2-cyano-6-hydroxybenzothiazole as well as boronic compounds, such as those disclosed in U.S. Pat. No. 5,629,168, incorporated herein by reference in its entirety, including, 4-iodophenylboronic acid (PIMA), 4-bromophenylboronic acid (PBBA), 4-chlorophenylboronic acid, 3-chlorophenylboronic acid, 3,4-dichlorophenylboronic acid, 2,3-dichlorophenylboronic acid, 5-bromo-2-methoxybenzeneboronic acid, 3-nitrophenylboronic acid, 4-chloro-3-nitrophenylboronic acid, 3-aminophenylboronic acid, 3-amino-2,4,6-trichlorophenylboronic acid, 4-(2'-carboxyethenyl)phenylboronic acid, 1-naphthaleneboronic acid, 6-hydroxy-2-naphthaleneboronic acid, phenylboronic acid, 2-methylphenylboronic acid, 4-methylphenylboronic acid, dimethyl-phenylboronic acid, 4-bromophenyl-di-n-butoxyborane, 4-carboxy-3-nitrophenylboronic acid, 4-(trimethylsilyl)benzeneboronic acid, 4-biphenylboronic acid, 4-(phenoxy)benzeneboronic acid, 4-(3'-borono-4'-hydroxyphenylazo)benzoic acid, diphenylisobutoxyborane, 4-(4'-chloroanilino)phenylboronic acid, 4,4'-bis(phenylboronic acid), 4-(4'-bromophenyl)phenyl-di-n-butoxyborane, di(3',5'-dichlorophenoxy)-3,5-dichlorophenylborane, 4-chlorophenyl-di-(4'-chlorophenoxy)borane, pentaerythritol borate, boroglycine, 2-phenyl-1,3,2-dioxaborinane, bis (catechol)borate and 2-hydroxy-5-[(3'-trifluoromethyl)phenylazo]benzeboronic acid and diphenylboronic anhydride. Other enhancers include 6-hydroxybenzothiazole, substituted phenols, such as those disclosed in U.S. Pat. No. 4,598,044, incorporated herein by reference in its entirety; aromatic amines including those disclosed in U.S. Pat. No. 4,729,950, incorporated herein by reference in its entirety; and phenols substituted in ortho and/or para positions by imidazolyl or benzimidazolyl (U.S. Pat. No. 5,043,266, incorporated herein by reference in its entirety).

In some embodiments, the luminescent label will be a luciferase enzyme. Examples are luciferases isolated from a variety of luminous organisms, such as the luciferase genes of *Photinus pyralis* (the common firefly of North America), *Pyrophorus plagiophthlalainus* (the Jamaican click beetle), *Renilla reniformis* (the sea pansy), and several bacteria (e.g., *Xenorhabdus luminescens* and *Vibrio* spp). Luciferases are enzymes found in luminous organisms which catalyze luminescence reactions. They are organized into groups based on commonalities of their luminescence reactions. All luciferases within a group are derived from related luminous organisms, and all catalyze the same chemical reaction. Examples are beetle luciferases, which all catalyze ATP-mediated oxidation of the beetle luciferin; and anthozoan luciferases which all catalyze oxidation of coelenterazine (Ward W W and Cormier M J. *Proc Natl Acad Sci* 1975;72 (7):2530-4.). With the technical capabilities of molecular biology, it is possible to alter the structure of a luciferase found in nature to yield a functional equivalent thereof. A functional equivalent is an enzyme that maintains the ability to catalyze the same luminescence reaction, and thus it remains in the same group of enzymes. Luciferase as used herein is intended to include naturally occurring and non-naturally occurring luciferase enzymes.

Luciferases generate light via the oxidation of enzyme-specific substrates, called luciferins. For firefly luciferase and all other beetle luciferases, this is typically done in the presence of magnesium ions, oxygen, and ATP. For anthozoan luciferases, including *Renilla* luciferase, oxygen is required along with the luciferin. Additional reagents such as, for example, coenzyme A can be used to yield greater enzyme turnover and greater luminescence intensity.

It will be understood that other molecules that generate light by interaction with chemiluminescent reactants can be used in the present invention such as hemin which interacts with reactants such as luminol and peroxide and aequorin which interacts with calcium ion to generate luminescence.

The luminescent labels of the present invention can be made to luminesce without the addition of substrate or other reagents but by other means of exciting them, such as with light of the appropriate wavelength or electrochemical energy.

The performance of luminescent reactions, such as those described herein, can be improved by use of the nanostructures of the present invention. Although polymer enhancement of luminescent enzyme catalyzed reactions is known, the use of a modified nanoenvironment to enhance and better control the reaction has not been known heretofore.

Although any of the polymers disclosed herein can be used in connection with any of the luminescent labels, certain polymers will be preferred in combination with certain labels. Preferably, the polymers will be ones that modulate, e.g., enhance, the signal from enzyme catalyzed reaction. For example, for use with alkaline phosphatase catalyzed reactions, preferred polymers to be immobilized on the nanostructures include polyhydroxyacrylates, polyvinyl carbamate, methacrylate, polyvinylalkylethers, polyethylenesulfonic acid, polyacrylamideomethylpropanesulfonic acid, polyvinyl alcohol, polyvinylalkylpyrrolidinones, polyvinylalkyloxazolidones, BSA, nylon, and poly[vinylbenzyl(benzyldimethyl ammonium) chloride]. While not wishing to be bound by any particular theory, it is postulated that the role of the polymer is to provide a more hydrophobic environment for decomposition of the excited electronic state intermediate formed in the scission of the 1,2-dioxetane ring structure. The polymer can be optionally combined with fluorophores that then act as energy acceptors and emit light at a wavelength characteristic of the fluorophore. This effect can be seen, for example, with enzyme in solution or immobilized as part the detection conjugate in a sandwich assay. In both situations, the enzyme is a dynamic environment and interaction between the polymer and the enzyme or the products of the enzyme reaction are governed by the random motion of the polymer in solution. In an exemplary embodiment, the polymer-luminescent label nanostructures will preferably create a more ordered and/or more static nanoenvironment that will maximize polymer interactions. The enhancement effect can be improved by a tighter control of the nanoenvironment as provided by the present invention.

For use with peroxidase catalyzed reactions, preferred polymers to be immobilized on the nanostructures include hydroxypropyl methylcellulose, hydroxyethyl cellulose, and hydroxybutyl methylcellulose. Boronic or phenolic enhancers are generally used in combination with the horseradish peroxidase and its substrates. A polysorbate, such as Tween 20 can also be used to stabilize light emission from the horseradish peroxidase (HRP) catalyzed chemiluminescent oxidation of hydroxyaryl cyclic diacylhydrazides.

For use with luciferase catalyzed reactions, preferred polymers to be immobilized on the nanostructures include polyethylene glycol, polyvinylpyrrolidone, and dextran. While not wishing to be bound by any particular theory, it is postulated that the polymer is acting as a reservoir for the inhibitory oxyluciferin product and the reaction and thus constantly regenerating active firefly luciferase.

One way of improving the signal in an immunoassay or nucleic acid probe assay is to adopt a multi-label strategy. Various ways have been devised to improve the sensitivity of an assay by increasing the number of labels that signal a specific binding event. By utilizing a modified nanoenvironment in luminescent assays, increased labels per binding moiety can be combined with the increased efficiency of each label in order to provide a significant signal enhancement. Increasing the signal has several benefits. For example, more intense light signals are easier to measure and can be measured using relatively inexpensive detectors such as solid-state detectors and photographic film. In addition, an increase in signal without a concomitant increase in background improves the detection limits for the label. This in turn increases the detection limit for analytes detected using the label in assays such as, for example, sandwich-type of assay, and can facilitate non-amplification assays for nucleic acid targets.

A wide variety of assays exist which use light emission to determine the presence or concentration of a particular sample in a substance. The nanostructures described herein can be used in any of these assays.

Assays employing nanostructures of the present invention can include conventional assays, such as protein and nucleic acid assays (e.g., Southern, Northern and Western blot assays) DNA sequencing, ELISA, competitive assays, sandwich assays, agglutination types of assays, as well as other liquid phase and mixed phase assays performed on membranes and beads and other solid phases.

In general, the assays consist of an analyte, a nanostructure, and a luminescent label. In general, procedures are performed according to standard, well-known protocols. For example, in DNA assays, the target biological substance can be bound by a DNA probe with an enzyme covalently or indirectly linked thereto, the probe being admixed with the sample immobilized on a membrane, to permit hybridization. Thereafter, excess enzyme conjugate is removed, and substrate is added to the hybridized sample. If hybridization has occurred, the sample will luminesce.

In an exemplary embodiment, a nanostructure of the present invention can be used in a energy transfer competitive assay format. In one example, a nanostructure of the present invention specific for an analyte of interest and having a donor fluorophore associated with it will be added to a sample with a conjugate comprising a binding agent bound to an acceptor molecule. After incubation, the reaction mixture will be exposed to excitation light specific for the donor fluorophore. If a complex forms between the nanostructure and the binding agent conjugated to the acceptor molecule, the excited donor will transfer energy to the acceptor molecule. The acceptor molecule will them emit light at its characteristic frequency. Measurement of this light emission can provide an indication of the amount of analyte in the sample. Low analyte concentration will lead to a large signal whereas high analyte concentration will lead to a low signal.

In an alternative embodiment, a chemiluminescent label can be used as a light source to excite a fluorescent label. In one example, a nanostructure of the present invention specific for an analyte of interest will have a chemiluminescent label associated with it. The nanostructure will be added to the sample with a conjugate comprising a binding agent conjugated to an acceptor molecule, e.g., fluorophore. After incubation, the reaction mixture will be exposed to chemical trigger for the chemiluminescent label. If a complex forms between the nanostructure and the binding agent conjugated to the acceptor molecule, the acceptor will be excited by the incident radiation from the chemiluminescent label. The acceptor will then emit light at its characteristic frequency. Measurement of the light at the frequency emitted by the chemiluminescent label, and at the frequency emitted by the acceptor can provide an indication of the amount of analyte in the sample. Low analyte concentration will lead to a signal at the frequency of the acceptor whereas high analyte concentration will lead to a signal at the frequency of the chemiluminescent label.

In yet another alternative embodiment, a bioluminescent label can be used in a process known as bioluminescence resonance energy transfer. In bioluminescence resonance energy transfer, energy transfer occurs between luminescent donor and fluorescent acceptor proteins. As with fluorescent energy transfer, resonance energy transfer can occur when part of the energy of an excited donor is transferred to an acceptor protein which then emits light at a different wavelength (See, e.g., Boute et al., *Trends in Pharmacological Sciences* 2002;23:351-354; Issad et al., *Biochemical Pharmacology* 2002;64:813-817). In exemplary embodiments, a bioluminescent label can be used a light source to excite a second bioluminescent label.

Fluorescence resonance energy transfer (FRET) is a fluorescence-based assay method of detecting different types of biological interactions in homogeneous (non-separation) assay formats. Energy transfer can be achieved by the direct resonance interaction of the donor and an acceptor fluorophore. The intensity of the FRET signal can be related to the specific biological events, e.g., antigen-antibody, nucleic acid-nucleic acid, protein-DNA and protein-peptide interactions (Patel, L. R. et al. *Proc. Natl. Acad. Sci. USA*, 1994;91; 7360-7364), and report enzyme-mediated cleavage of DNA and peptide substrates (Nagase, H. et al. *J. Biol. Chem.,* 1994; 269, 20952-20957).

Signal generation in FRET generally requires that the donor probe should have a good quantum yield and the acceptor should have a large extinction coefficient. Preferably, there should be considerable overlap between the emission spectrum of the donor and the absorption spectrum of the acceptor. The use of a non-fluorescent dye as a quencher minimizes the intensity of emission from the matched donor dye. This allows either signal-decrease assays, where the donor and acceptor fluorophores are brought into close proximity to each other for example in a binding interaction, or signal-increase assays, which involve cleavage of dual-labeled substrates (e.g., TaqMan type assays)(Heid C A et al. *Genome Research.* 1996;6:986-94). Fluorophores such as the lanthanide chelates can also be used in FRET. These fluorophores have long fluorescence lifetimes compared with common organic fluorophores. Hence, sources of short-lived background fluorescence can be gated out by the detector, thus increasing the signal-to-noise ratio (Jones, S. G. et al. *J. Fluorescene* 2001;11, 13-21; Li, M. and Selvin, P. R. *Bioconjug. Chem.,* 1997;8, 127-132). Applications of FRET include measurement of distance between sites or macromolecules (Wu P, Brand L. *Anal Biochem* 1994;218:1-13), DNA hybridization (N. Ota, et al., *Nucleic Acid Res.* 26 (3) (1998) 735-743), detection of DNA amplification (Heid et al., *Genome Research.* 1996;6:986-94), DNA sequencing (Y. Li, A. N. Glazer, *Bioconjug. Chem.* 1999;10: 241-245), molecular beacon-based assays (Tan W. Wang K. Drake T J. *Current Opin-* ion in *Chemical Biology.* 2004; 8(5):547-53; S. Tyagi, F. R. Kramer, *Nat. Biotechnol.* 1996;14 :303-308), immunoassay (E. F. Ullman, M. Schwarzberg, K. E. Rubenstein, *J. Biol. Chem.* 1976;251: 264-270), protein-protein interactions (Parsons M. Vojnovic B. Ameer-Beg S. *Biochemical Society Transactions.* 2004;32:431-3), protein conformational changes (Truong K. Ikura M. *Current Opinion in Structural Biology.* 2001;11:573-8), physiological indicators and sensors (Rolinski et al. *Appl Phys Lett* 2001;78:2796-8), and drug discovery (Milligan G. *European Journal of Pharmaceutical Sciences.* 2004;21(4):397-405).

In exemplary assays of the present invention that use energy transfer, either one of or both the donor and acceptor molecules can be directly or indirectly conjugated to a nanostructure of the present invention.

In certain embodiments, the nanostructures of the present invention can comprise fluorescent labels adjacent to chemiluminescent enzymes. In some such embodiments, the chemiluminescent enzyme will catalyze the decomposition of a substrate giving off energy that is transferred to the fluorescent molecule resulting in the emission of a specific wavelength of light in a different part of the spectrum and thus providing a chemical source of energy for fluorescent emission. In an exemplary embodiment, an assay system can, for example, have multiple types of layer-by-layer structures, each of which contains the same chemiluminescent enzyme, but a different fluorescent molecule. Thus, all of the structures would utilize the same chemiluminescent substrate, but would have different emission signatures. In an exemplary capture type assay, each analyte of interest can be associated with a different fluorescent molecule, thus the detection of a specific fluorescent molecule will indicate the presence of a specific analyte.

In one particular embodiment, for example, a polymer nanostructure assembled by layer-by-layer technique comprising two layer-by-layer structures is constructed. The first layer is fabricated with, for example, a fluorescent molecule that emits at 500 nm and has an outermost layer coated with a binding moiety, such as PSA specific oligonucleotides; the second is fabricated with, for example, a fluorescent molecule that emits at 700 nm and has an outermost layer coated with a binding moiety, such as CEA specific oligonucleotides. When these two structures are mixed together in the presence of CEA oligonucleotide target, only the CEA oligonucleotide coated structure will be captured; the PSA oligonucleotide coated structure can be washed away. When the captured CEA oligonucleotide coated structure is exposed to substrate, the chemiluminescent enzyme catalyzes the decomposition of substrate. The byproducts of the substrate result in excitation of the fluorescent molecule which emits at 700 nm. Thus, detection a 700 nm emission indicates the presence of captured CEA oligonucleotide coated structures. One alternative format to the assay would be to simultaneously detect multiple analytes. In this example, both CEA and PSA oligonucleotide coated structures would be coated. The addition of substrate results in emission at both 500 nm and 700 nm. By using two separate detectors; each with filters specific for either 500 nm or 700 nm, the presence of both CEA and PSA oligonucleotide coated structures can be detected and measured simultaneously.

The assays of the invention can be practiced with some components in solution. In certain embodiments, one or more components can be substantially insoluble in the assay medium. In an exemplary embodiment, one or more members selected from the group consisting of the binding moiety, the binding partner and the analyte are attached to a surface. Useful surface include, but are not limited to, glass or polymeric beads, sheets, fibers, membranes (e.g. nylon, nitrocellulose), slides (e.g. glass, quartz), chips, silver island films (Lakowicz et al., *Biochem Biophys Res Commun* 2001; 286: 875-9; Lakowicz et al., *Anal Biochem.* 2002; 301: 261-277) and the like.

The nanostructures of the present invention can be utilized in a microarray format. The nanostructures themselves be components of a microarray or, alternatively they can be utilized as a tool to screen components of a microarray. Thus, the present invention provides a method of screening a microarray. The method can include contacting the members of the microarray with a nanostructure of the present invention and interrogating the microarray for regions of luminescence. The luminescent regions are indicative of the presence of an interaction between the binding moiety and a microarray component. In another version of this method, the microarray is interrogated for regions in which luminescence is quenched, again indicating the presence of an interaction between the binding moiety and a component of the microarray.

These assay techniques provide the ability to detect both the presence and amount and concentration of small quantities of analytes and are useful in many application, for example medical diagnostics and forensic applications. Other applications include, for example, drug discovery, reporter-gene assays to monitor gene expression, second-messenger quantitation, protein kinase assays, antagonist/agonist screening, and protein-protein interaction analysis. As described, the present invention provides methods for detecting target nucleic acids in a sample. By "sample" is intended any sample obtained or derived from an individual, body fluid, cell line, tissue culture, or other source, including the environment, which contains or is suspected of containing the analyte of interest. As indicated, biological samples include body fluids (such as lymph, sera, plasma, urine, semen, expired air, synovial fluid and spinal fluid) and tissue sources. Methods for obtaining tissue biopsies and body fluids from mammals are well known in the art. Methods for obtaining environmental samples are also well known in the art.

Luminescence can be detected using conventional means, for example, a photomultiplier tube detector, camera luminometer, or even the naked eye. Luminescence intensity can be measured to determine the concentration of the substrate. The light emission of membrane-based assays can be imaged, for example, with standard x-ray film or Polaroid instant photographic film. Acquisition of digitized images can be accomplished, for example, with a phosphor storage screen and CCD camera instrumentation.

Luminescent signals generated in microplate-based assays can be quantified with a variety of commercially available luminometers. Such luminometers are normally instruments based on photomultiplier tube (PMT) technology, which move each well of the microplate directly below the PMT detector or the lens/fiber-optic light-collection interface. Sensitive detection of chemiluminescent signals in 96-well and higher-density microplates and microarrays is also possible with CCD camera instrumentation. Methods of detecting and quantitating luminescent labels are well known to those of skill in the art.

In an exemplary embodiment of the present invention, the analyte to be detected will be mRNA transcripts of a tumor antigen, such as prostate specific antigen ("PSA"). In one such embodiment, PSA mRNA can be detected by PSA-mRNA specific oligonucleotide probes linked to biotin. The biotin-linked probes will conjugate to streptavidinylated linked nanostructure of the present invention. Bound conjugate can be measured using a substrate for the luminescent label conjugated to the polymer loaded nanostructure.

As also described, the present invention provides methods for detecting hormones in a biological sample. In an exemplary embodiment of the present invention, the analyte to be detected will be a hormone, such as thyrotropin, anterior pituitary hormone ("TSH"). In one such embodiment, TSH can probed by an anti-TSH antibody bound to biotin. The biotin-linked probes will conjugate to streptavidinylated linked nanostructure of the present invention. Bound conjugate can be measured using a substrate for the luminescent label conjugated to the polymer loaded or fabricated nanostructure.

The present invention also provides kits for conducting an assay for the presence or concentration of an analyte. The kits of the present invention comprise a nanostructure of the present invention, i.e., a polymer loaded nanostructure or polymer fabricated nanostructure or combination thereof associated with a luminescent label and a substrate capable of interacting with the luminescent label.

In some embodiments, the kits will comprise a nanostructure of the present invention associated with a phosphatase or peroxidase enzyme, and a 1,2 dioxetane capable of interacting with the luminescent label. The kit can further comprise, for example, a hydrophobic fluorometric substrate for the enzyme, and optionally an enhancer molecule capable of improving fluorescence.

In some embodiments, the kits will comprise a nanostructure of the present invention associated with a peroxidase enzyme; a dihydrophthalazinedione; and a peroxide compound in an amount which reacts with the dihydrophthalazinedione in the presence of the peroxidase. The kit can optionally comprise any one or more of an enhancer compound in an amount which enhances light production from the dihydrophthalazinedione in the presence of the peroxidase enzyme and/or decreases background chemiluminescence; a chelating agent in an amount which prevents the peroxide compound from activating the dihydrophthalazinedione prior to reaction with the peroxidase; a chemiluminescence enhancing surfactant; and a solid support on which the reaction is performed.

In some embodiments, the kits will comprise a nanostructure of the present invention associated with a luciferase enzyme; a luciferin; Mg; and ATP.

In embodiments wherein the kit further comprises a binding moiety conjugated to the nanostructure, the kits can further comprise a labeled detector probe capable of binding to the analyte of interest and the binding moiety conjugated to the nanostructure.

Methods for the Production of Nano-Sized Tube and Rods

The present invention provides, inter alia, methods for the production of nano-sized tube and rods, including arrays of nanotubes and nanorods from a nylon. In particular, the present inventors have discovered that nano-sized tubes and rods can be fabricated from nylon using template synthesis methods.

Any nylon can be used in the present invention to make the nanotubes and nanorods. The term nylon, as used herein, refers to a polyamide material and includes pure nylon as well as composites of nylon. The nylon used in the present invention can vary widely in crystallinity or solid structure, melting point, and other physical properties.

Polyamides include homopolymers, copolymers, blends and grafts of synthetic long-chain polyamides having recurring amide groups in the polymer main chain as an essential constituent. Examples of such polyamides are nylon-6 (polycaprolactam), nylon-6,6 (polyhexamethyleneadipamide), nylon-4,6 (polytetramethyleneadipamide), nylon-6,10 (polyhexamethylenesebacamide), nylon-7 (polyenantholactam), nylon-11 (polyundecanolactam), nylon-12 (polydodecanolactam). As well as polyamides known by the generic name of nylon, polyamides further include the aramids (aromatic polyamides), such as poly-meta-phenyleneisophthalamide (NOMEX® fiber, U.S. Pat. No. 3,287,324) or poly-para-phenyleneterephthalamide (KEVLAR® fiber, U.S. Pat. No. 3,671,542).

Methods of preparing polyamides are known in the art and include, for example, the following methods described in U.S. Pat. No. 6,958,381.

In a polymerization from dicarboxylic acids and diamines and also in a polymerization from amino acids or their derivatives, such as aminocarbonitriles, aminocarboxamides, aminocarboxylate esters or aminocarboxylate salts, the amino and carboxyl end groups react with one another to form an amide group and water. The water can subsequently be removed from the polymer.

In a polymerization from carboxamides, the amino and amide end groups of the starting monomers or starting oligomers react with one another to form an amide group and ammonia. The ammonia can subsequently be removed from the polymer. This polymerization reaction is customarily known as a polycondensation.

A polymerization from lactams as starting monomers or starting oligomers is customarily known as a polyaddition. Starting monomers can include, for example lactams, omega-aminocarboxylic acids, omega-aminocarboxamides, omega-aminocarboxylate salts, omega-aminocarboxylate esters, equimolar mixtures of diamines and dicarboxylic acids, dicarboxylic acid/diamine salts or mixtures thereof.

Useful monomers include, for example, monomers or oligomers of a $C_2$ to $C_{20}$, preferably $C_2$ to $C_{18}$, arylaliphatic or, preferably, aliphatic lactam such as enantholactam, undecanolactam, dodecanolactam or caprolactam, in particular caprolactam; monomers or oligomers of $C_2$ to $C_{20}$, preferably $C_3$ to $C_{18}$, aminocarboxylic acids such as 6-aminohexanoic acid or 11-aminoundecanoic acid, and dimers, trimers, tetramers, pentamers or hexamers thereof, and salts thereof such as alkali metal salts, for example lithium, sodium or potassium salts; monomers or oligomers of $C_2$ to $C_{20}$ amino acid amides such as 6-aminohexanamide or 11-aminoundecanamide, and dimers, trimers, tetramers, pentamers or hexamers thereof; esters, preferably $C_1$-$C_4$ alkyl esters, such as methyl, ethyl, n-propyl, i-propyl, n-butyl, i-butyl or s-butyl esters, of $C_2$ to $C_{20}$, preferably $C_3$ to $C_{18}$, aminocarboxylic acids, such as 6-aminohexanoic acid esters, for example methyl 6-aminohexanoate, or 11-aminoundecanoic acid esters, for example methyl 11-aminoundecanoate; monomers or oligomers of a $C_2$ to $C_{20}$, preferably $C_2$ to $C_{12}$, alkyldiamine, such as tetramethylenediamine or, preferably, hexamethylenediamine, with a $C_2$ to $C_{20}$, preferably $C_2$ to $C_{14}$, aliphatic dicarboxylic acid such as sebacic acid, dodecanedioic acid or adipic acid, and dimers, trimers, tetramers, pentamers or hexamers thereof; monomers or oligomers of a $C_2$ to $C_{20}$, preferably $C_2$ to $C_{12}$, alkyldi amine, such as tetramethylenediamine or, preferably, hexamethylenediamine, with a $C_8$ to $C_{20}$, preferably $C_8$ to $C_{12}$, aromatic dicarboxylic acid or derivatives thereof, for example chlorides, such as naphthalene-2,6-dicarboxylic acid, preferably isophthalic acid or terephthalic acid, and dimers, trimers, tetramers, pentamers or hexamers thereof; monomers or oligomers of a $C_2$ to $C_{20}$, preferably $C_2$ to $C_{12}$, alkyldiamine, such as tetramethylenediamine or, preferably, hexamethylenediamine, with a $C_9$ to $C_{20}$, preferably $C_9$ to $C_{18}$, arylaliphatic dicarboxylic acid or derivatives thereof, for example chlorides, such as o-, m-or p-phenylenediacetic acid, and dimers, trimers, tetramers, pentamers or hexamers thereof; monomers or oligomers of a $C_6$ to $C_{20}$, preferably $C_6$ to $C_{10}$, aromatic diaamine, such as m-or p-phenylenediamine, with a $C_2$ to $C_{20}$, preferably $C_2$ to $C_{14}$, aliphatic dicarboxylic acid such as sebacic acid, dodecanedioic acid or adipic acid, and dimers, trimers, tetramers, pentamers or hexamers thereof; monomers or oligomers of a $C_6$ to $C_{20}$, preferably $C_6$ to $C_{10}$, aromatic diamine, such as m-or p-phenylenediamine, with a $C_8$ to $C_{20}$, preferably $C_8$ to $C_{12}$, aromatic dicarboxylic acid or derivatives thereof, for example chlorides, such as naphthalene-2,6-dicarboxylic acid, preferably isophthalic acid or terephthalic acid, and dimers, trimers, tetramers, pentamers or hexamers thereof; monomers or oligomers of a $C_6$ to $C_{20}$, preferably $C_6$ to $C_{10}$, aromatic diamine, such as m-or p-phenylenediamine, with a $C_9$ to $C_{20}$, preferably $C_9$ to $C_{18}$, arylaliphatic dicarboxylic acid or derivatives thereof, for example chlorides, such as o-, m-or p-phenylenediacetic acid, and dimers, trimers, tetramers, pentamers or hexamers thereof; monomers or oligomers of a $C_7$ to $C_{20}$, preferably $C_8$ to $C_{18}$, arylaliphatic diamine, such as m-or p-xylylenediamine, with a $C_2$ to $C_{20}$, preferably $C_2$ to $C_{14}$, aliphatic dicarboxylic acid such as sebacic acid, dodecanedioic acid or adipic acid, and dimers, trimers, tetramers, pentamers or hexamers thereof; monomers or oligomers of a $C_7$ to $C_{20}$, preferably $C_8$ to $C_{18}$, arylaliphatic diamine, such as m-or p-xylylenediamine, with a $C_6$ to $C_{20}$, preferably $C_6$ to $C_{10}$, aromatic dicarboxylic acid or derivatives thereof, for example chlorides, such as naphthalene-2,6-dicarboxylic acid, preferably isophthalic acid or terephthalic acid, and dimers, trimers, tetramers, pentamers or hexamers thereof; monomers or oligomers of a $C_7$ to $C_{20}$, preferably $C_8$ to $C_{18}$, arylaliphatic diamine, such as m-or p-xylylenediamine, with a $C_9$ to $C_{20}$, preferably $C_9$ to $C_{18}$, arylaliphatic dicarboxylic acid or derivatives thereof, for example chlorides, such as o-, m-or p-phenylenediacetic acid, and dimers, trimers, tetramers, pentamers or hexamers thereof, and homopolymers, copolymers, mixtures and grafts of such starting monomers or starting oligomers.

Lactams are obtainable, for example, by reacting a cyclic ketone with hydroxylamine to form the corresponding oxime and a subsequent Beckmann rearrangement or from the corresponding aminonitriles by hydrolytic cyclization before or during the polymerization, especially in the presence of catalysts, such as titanium dioxide, in a conventional manner.

The production of omega-aminocarboxylic acids, omega-aminocarboxamides, omega-aminocarboxylate salts and omega-aminocarboxylate esters is known. They are obtainable for example from the corresponding aminonitriles before or during the polymerization. The preparation of dicarboxylic acids is known. They are obtainable for example from the corresponding dinitriles before or during the polymerization. Diamines may be prepared in a conventional manner, as by hydrogenation of the corresponding dinitriles.

Exemplary nylons for use in the present invention include, for example, polyamide resins having a ratio of methylene ($CH_2$) to amide (NHCO) groups within a range of about 5:1 to about 20:1, most preferably from about 5:1 to about 10:1. Particularly preferred nylons for use in the present invention include, for example, nylon 6; nylon 6,6; nylon 6,9; nylon 6,10; nylon 6,12; nylon 11; nylon 12; and nylon 6(3)T. It will be understood that nylon polymers are available in a wide variety of grades, which vary appreciable with regard to molecular weight.

The nanotubes and nanorods of the present invention fabricated from nylon are typically from about 10 nanometers to about 100 microns in length, preferably from about 6 microns to about 60 microns in length, and more preferably from about 6 microns to about 11 microns in length. In certain embodiments, they nanotubes and nanorods can be less than 1000 nanometers in length, or even less than 800, 700, 600, 500, 400, 300, 200, 100, or 50 nanometers in length.

The nanotubes are hollow structures comprising a nylon outer wall surrounding an unfilled space, e.g., a cavity. The nanorods are a solid nylon structure. The nanotubes and nanorods of the present invention fabricated from nylon are generally from about 1 nanometer to about 1000 nanometers in outer diameter, preferably from about 10 nanometers to about 800 nanometers in outer diameter, more preferably from about 10 nanometers to about 500 nanometers in outer diameter, and even more preferably about 10, about 20, about 30, about 40, about 50, about 60, about 80, about 90, about 100, about 200, about 300, about 400, or about 500 nanometers in outer diameter. In certain embodiments, the outer diameter is less than about 500 nanometers or less than about 100 nanometers.

Accordingly, in certain embodiments, the dimensions of the nanorods and nanotubes of the present invention will be from about 10 nanometers to about 100 microns in length, preferably from about 6 microns to about 60 microns in length, and more preferably from about 6 microns to about 11 microns in length and from about 1 nanometer to about 1000 nanometers in outer diameter, preferably from about 10 nanometers to about 800 nanometers in outer diameter, more preferably from about 10 nanometers to about 500 nanometers in outer diameter, and even more preferably about 10, about 20, about 30, about 40, about 50, about 60, about 70, about 80, about 90, about 100, about 200, about 300, about 400, or about 500 nanometers in outer diameter.

Outer diameter as used herein is a transverse cross-section dimension. For a tube or rod of circular cross-section it is the length of a straight line which passes through the center of the tube or rod, and terminates at the outermost circumference. For nanotubes and nanorods of non-circular transverse cross section, outer diameter refers to the largest cross-sectional dimension.

The nanotubes and nanorods can be composed of a variety of shapes in profile as well as in cross-section. The shape can be diverse, including: tube, cone, oblong, cube, prism, pyramid, horn. The resulting profile or cross-section may be circular, rectangular, square, elliptical, hexagonal, pentagonal, trapezoidal, or other regular or irregular cross-sections.

The present invention utilizes template synthesis methods to create nanotubes and nanorods from nylon within the pores of a casting mold. In certain embodiments, the nanotubes and rods will be non-porous.

The casting mold can be any mold that will remain intact during molding and can be selectively removed (e.g., physically or chemically) after molding to harvest the nanotubes or nanorods. For example, in embodiments wherein molten nylon is used, the casting mold will be any mold that has a melting point above the melting point of the nylon and can be removed without affecting the integrity of the nylon within in its pores. In embodiments wherein nylon dope is used, the casting mold will be any mold that can withstand the volatile solvent and can be removed without affecting the integrity of the nylon within its pores. The casting molds of the present invention have pore features within which the nylon solidifies. As used herein, the term "pore features" not only refers to pores that penetrate through the mold but also indentations, including etchings and posts, within the mold that may not penetrate all the way through the mold. Exemplary casting membranes with pore features, as herein defined, include, for example, oxidized metals, such as aluminum oxide, also referred to as alumina, e.g., anodic aluminum oxide, track etched polymers fabricated from polycarbonate, polyester, or other materials that are amenable to track etching, nanochannel glass arrays, zeolites, wax surface indented by nanoscale tip, oxidized silicon, silicon nitride, and polymethyl-methacrylate. (See, e.g., Sitti, et al., Proceedings of the 2003 IEEE/ASME, International Conference on Advanced Intelligent Mechatronics, 2006, 886-890; Komarov et al., Vacuum 78, 2005, 361-366; Heyderman et al., Fabrication of Cusomised Nanopore Membrane Chips, PSI Scientific Report, 2002 Vol. VII; Li et al., Nature 2001, 412; 166-169; Schift et al., Microelectric engineering, 2000, 53:171-174; Tiefenauer et al., Ultrathin Nanopore Membranes for Bioanalysis, PSI Annual report 2001; Fleisher et al., Nuclear Tracks in Solids, Berkley, Univ. California Press, 1975; Tonucci et al., *Science* 1992, 252:783; Wu et al., *J Am Chem Soc* 1992; 114;10834).

In certain embodiments, the pores of the casting mold or template are generally from about 1 nanometer to about 1000 nanometers in diameter, preferably from about 10 nanometers to about 800 nanometers in diameter, more preferably from about 10 nanometers to about 500 nanometers in diameter, and even more preferably about 10, about 20, about 30, about 40, about 50, about 60, about 70, about 80, about 90, about 100, about 200, about 300, about 400, or about 500 nanometers in diameter. The outer diameter of the nanotube and nanorods will be determined by the diameter of the pore features of the casting mold, and the length of the nanotubes and nanorods will be determined by the thickness of the casting mold. Accordingly, a casting mold having pore features 200 nanometers in diameter and a thickness of 600 microns will be used to create a nanotube with an outer diameter of 200 nanometers and 600 microns in length. Table 1 below provides dimensions for exemplary molds having pore features.

TABLE 1

| Mold | Pore Diameter (nanometers) | Template thickness (microns) |
|---|---|---|
| Alumina | 20 | 60 |
| | 100 | 60 |
| | 200 | 60 |
| Polycarbonate | 10 | 6 |
| | 30 | 6 |
| | 50 | 6 |
| | 80 | 6 |
| | 100 | 6 |
| | 200 | 10 |
| | 400 | 10 |
| | 600 | 9 |
| | 800 | 9 |
| | 1000 | 11 |
| Polyester | 100 | 6 |
| | 200 | 10 |
| | 400 | 10 |
| | 600 | 9 |
| | 800 | 9 |
| | 1000 | 11 |

In certain methods of the present invention, the nanorods and nanotubes are prepared by heating nylon in a presence of a casting mold having pore features to a temperature at or above the melting point of the nylon, cooling the casting mold having the nylon within its pores, and removing the casting mold to provide the nanotubes or nanorods. Heating the nylon in the presence of the casting mold causes the nylon melt to enter into the pores of the mold. Typically, capillary force and adhesive forces between the template and the melt cause the melt to enter into the pores, although other forces can be used to cause the melt to enter in the pores of the casting mold. In certain embodiments, the melting is performed at a temperature of from about 200° C. to about 300° C. In certain embodiments, the melting is performed under an inert gas to prevent oxidation and browning. After the melt enters the pores, the casting mold containing the nylon melt within its pores is cooled so that the nylon solidifies within the pores. Following solidification of the nylon, the casting mold is removed to provide the nanotubes or nanorods.

Preferably, the casting mold is dissolved in a solvent, however, other methods of removing the casting mold can be used. These methods include, for example, mechanical force or degradation, sonication, free-thaw fracture, mild heating (for example, in the case of a wax casting mold), and mechanical peeling. Exemplary solvents for dissolving alumina casting membranes include, for example sodium and potassium hydroxide.

Exemplary nylons and their melting points are provided in Table 2 below.

TABLE 2

| Name | Structure | Melting point ° C. |
|---|---|---|
| Nylon 6 | —NHCO(CH$_2$)$_5$— | 220 |
| Nylon 6,6 | —NH(CH$_2$)$_6$NHCO(CH$_2$)$_4$CO— | 255 |
| Nylon 6,9 | —NH(CH$_2$)$_6$NHCO(CH$_2$)$_7$CO— | 210 |
| Nylon 6,10 | —NH(CH$_2$)$_6$NHCO(CH$_2$)$_8$CO— | 215 |
| Nylon 6,12 | —NH(CH$_2$)$_6$NHCO(CH$_2$)$_{10}$CO— | 250-260 |
| Nylon 11 | —NH(CO)(CH$_2$)$_{10}$— | 185 |
| Nylon 12 | —NH(CO)(CH$_2$)$_{11}$— | 178 |
| Nylon 6(3)T | —NH(CH$_2$CHMeCH$_2$CMe$_2$(CH$_2$)$_2$NHCOC$_6$H$_4$CO— | 250 |

In alternative methods of the present invention, the nanorods and nanotubes are prepared by dissolving nylon in a volatile solvent to create a nylon dope, applying the nylon dope to a casting mold having pore features, and removing the casting mold to provide the nanorod or nanotubes. The nylon dopes which can be used include solutions of nylon in various volatile solvents including, for example, lower alkanols, e.g., methanol, ethanol and butanol, including mixtures thereof or acids, for example, formic acid, citric acid, acetic acid, maleic acid and other acids which react with nylons through protonation of nitrogen in the amide group. Exemplary solvents include, for example, o-chlorophenyl, m-cresol, sulfuric acid, nitric acid, trichloroethanol, DMF, and formic acid. The solvent generally will be able to penetrate into the pores of the casting mold, yet evaporate before formation of the nanotubes or nanorods, e.g., by simple evaporation or under vacuum. The nylon dope is applied to a casting mold having pore features and enters into the pores of the casting mold. The nylon dope can be applied to the casting mold using any method that facilitates the entry of the nylon dope into the pores. These methods include, for example, vacuum filtration, soaking (e.g., by placing mold on top of the dope), dipping (e.g., by dipping the mold into the dope and letting excess dope drip off the saturated mold), pipetting, centrifugation, and the like. After the nylon dope is solidified therein, the casting mold is removed to provide the nanotubes or nanorods. Preferably, the casting mold is dissolved in a solvent, however, other methods of removing the casting mold can be used. These methods include, for example, mechanical force or degradation, sonication, free-thaw fracture, mild heating (for example, in the case of a wax casting mold), and mechanical peeling. Exemplary solvents for dissolving alumina casting molds include, for example sodium and potassium hydroxide. The skilled practitioner will understand that the choice of solvent for dissolving the casting mold depends on the solubility of the nylon in any given solvent. Exemplary volatile solvents for pairing with exemplary nylons for creating the nylon dope are provided in Table 3 below.

TABLE 3

| Name | Structure | Exemplary solvents |
|---|---|---|
| Nylon 6 | —NHCO(CH$_2$)$_5$— | o-chlorophenyl, m-cresol |
| Nylon 6,6 | —NH(CH$_2$)$_6$NHCO(CH$_2$)$_4$CO— | m-cresol |
| Nylon 6,9 | —NH(CH$_2$)$_6$NHCO(CH$_2$)$_7$CO— | m-cresol, sulfuric acid, nitric acid |
| Nylon 6,10 | —NH(CH$_2$)$_6$NHCO(CH$_2$)$_8$CO— | m-cresol, trichloroethanol |
| Nylon 6,12 | —NH(CH$_2$)$_6$NHCO(CH$_2$)$_{10}$CO— | m-cresol, trichloroethanol |
| Nylon 11 | —NH(CO)(CH$_2$)$_{10}$— | m-cresol |
| Nylon 12 | —NH(CO)(CH$_2$)$_{11}$— | m-cresol |
| Nylon 6(3)T | —NH(CH$_2$CHMeCH$_2$CMe$_2$(CH$_2$)$_2$NHCOC$_6$H$_4$CO— | DMF, formic acid, sulfuric acid |

In certain embodiments of the present invention, additional additives can be present in the nylon or nylon composite or added to the molten nylon or nylon dope to confer particular properites to the nylon nanotubes and rods. For example, these additives can be added to confer magnetic, optical, structural, frictional or radioactive properties to the nanotubes and rods. They can also be added to confer additional strength to the nanotubes and nanorods. Exemplary additives include, for example, magnetic powder, biological agents, such as for example, nucleic acids, and proteins, toughening agents, stabilizers, radioactive compounds, lubricants, such as, for example, molybdenum disulfide, pigments, dyes, fluorescent compounds, flame-retardant additives, for example, brominated styrene oligomers, reinforcements, such as, for example, glass fiber, carbon fiber, and aramid fiber, and nanoparticles, including metallic, organic and inorganic nanoparticles.

The present invention provides, inter alia, nanotubes and nanorods prepared by the methods described herein. The present invention also provides methods of using the nanotubes and nanorods prepared by the methods described herein in a variety of applications, including, for example, in luminescent assays.

Although the foregoing invention has been described in detail by way of example for purposes of clarity of understanding, it will be apparent to the artisan that certain changes and modifications are comprehended by the disclosure and can be practiced without undue experimentation within the scope of the appended claims, which are presented by way of illustration not limitation. The disclosures of all publications, patents and patent applications cited herein are hereby incorporated by reference in their entirety and for all purposes.

EXAMPLES

Example 1

Exemplary Method of Immobilizing Enzyme Labels on/in Polymer Nanotubes and Detecting Luminescence Enzyme adsorption will be achieved by mixing a solution of alkaline phosphatase (1 ug/mL) in 10 mM phosphate buffer (pH 7) with the nylon nanotubes for 1 hour at room temperature, followed by extensive washing to remove unbound enzyme. A similar procedure will be used for horseradish peroxidase and for firefly luciferase in view of the known inactivation of firefly luciferase by covalent coupling methods.

Nylon nanotubes were prepared using the membrane wetting method. One and a half nylon membrane filters (0.45 um-13 mm) (Whatman International Ltd., UK) were dissolved in 100 uL of formic acid 95% to form a nylon dope. A 200 nm pore diameter, a 100 nm pore diameter and a 20 nm pore diameter anodic aluminum oxide membrane (Whatman International Ltd., UK) were placed on a microscope slide and then 20 uL of the nylon solution was placed on each anodic membrane. The membranes changed from white to translucent but 5 minutes later, when the formic acid has evaporated they returned to their original white appearance. The individual membranes were submerged in sodium hydroxide (1 M) for 24 hours and then washed and dried. Alternatively, the nylon dope can be vacuum filtered through anodic aluminum oxide membrane or the nylon solution can be placed on a microscope slide and placed in contact with the membrane. Optionally, the upper layer of the membrane can be vacuum polished to remove the surface layer of polymer prior to dissolving the membrane. The nylon can be, for example, in the form of a thin membrane or can be a nylon dope that is allowed to evaporate to form a very thin film on nylon on, for example, a glass surface.

Methods that do not rely on the solubility of the nylon in a solvent are also available. A small amount of nylon was placed on a hot plate and melted. The membrane was placed in contact for several minutes such that the molten polymer was taken up into the pores of the membrane. After cooling the membrane was dissolved away.

Alkaline phosphatase will be attached to nylon nanotubes by covalently coupling to amino groups on the nylon surface nanotube surface using glutaraldehyde or 1-ethyl-3-(3-dimethyl aminopropyl)carbodiimide (EDAC). Initially, the nylon surface of the nanotube is hydrolyzed by treating the nylon with a solution of calcium chloride in methanol followed by hydrolysis at elevated temperature using 3.6 M hydrochloric acid. (Inman and Hornby, 1972) to produce free amine and carboxyl groups. A suspension of the nylon nanotubes (50 mg) is treated with glutaraldehyde (12.5% w/w) in 0.1 M, pH 8.6 sodium borate buffer and for 1.5 hour at 50° C. and then washed with the borate buffer. The activated nanotubes are then exposed to alkaline phosphatase (5 U/mL) in 0.2 M, pH 7.8 phosphate buffer) for 24 h at 0-4° C. Unreacted aldehyde groups on the nanotubes are then blocked with a 0.1M, pH 10 glycine/sodium hydroxide solution overnight at 0-4° C., followed by extensive washing to remove unbound enzyme. Alternatively, a suspension of the nylon nanotubes (50 mg) will be treated with EDAC (100 mM) and NHS (100 mM) for 1 hour at room temperature and then the activated nanotubes exposed to alkaline phosphatase (5 U/mL) at pH 8.5, followed by extensive washing to remove unbound enzyme.

Enzyme adsorption of horseradish peroxidase and firefly luciferase will be achieved by mixing a solution of horseradish peroxidase or firefly luciferase (1 ug/mL) in 10 mM phosphate buffer (pH 7) with the nanotubes for 1 hour at room temperature, followed by extensive washing to remove unbound enzyme. Horseradish peroxidase will be attached to nylon nanotubes by covalently coupling to amino-PEG surface nanotube surface using glutaraldehyde or 1-ethyl-3-(3-dimethyl aminopropyl)carbodiimide (EDAC).

Immobilized alkaline phosphatase will be measured by mixing a 5 uL sample of the nanotubes with 100 uL of a detection reagent comprising AMPPD (0.004 mmol/L) in 0.05 mol/L carbonate-1 mmol/L magnesium chloride buffer (pH 9.5).

Immobilized horseradish peroxidase will be measured by mixing a 5 uL sample of the nanotubes with 100 uL of a detection reagent comprising luminol (Sigma; sodium salt, 1.25 mmol/L)-peroxide (2.7 mmol/L) in Tris buffer containing 4-bromophenylboronic acid (0.1 mmol/L).

Immobilized firefly luciferase will be measured by mixing a 5 uL sample of the nanotubes with 100 uL of a detection reagent comprising firefly luciferin (1 mmol/L)-ATP (0.02 mol/L)-magnesium (0.1 mol/L) in glycylglycine buffer (0.025 mol/L, pH 7.8).

The enzyme loaded polymer nanotubes will generally be linked to a component of a binding reaction in order to be used in an immunoassay or DNA probe assay. The nanotube labels will be linked to biotin and streptavidin because the resultant streptavidinylated nanotubes and biotinylated nanotubes are universal conjugates that can be used in immunoassay or DNA probe assays.

Alkaline phosphatase and streptavidin or anti-TSH antibody (mouse) will be physically co-immobilized by incubating a suspension of the nylon nanotubes with a mixture of these two proteins.

Alkaline phosphatase and an amino-biotin derivative (e.g., 5-(biotinyamido)pentylamine or biotin-PEO-amine) will be attached to hydrolyzed nylon nanotubes by covalently coupling using glutaraldehyde. An alternative procedure would involve covalent coupling of a mixture of the amino-biotin derivative and strepatavidin to carboxyl groups on the nylon nanotube surface using 1-ethyl-3-(3-dimethyl aminopropyl) carbodiimide and NHS at pH 8.5 (Wang 2004).

The presence of biotin groups or streptavidin groups on the polymer nanotubes will be demonstrated by binding of fluorescein-avidin, fluorescein-streptavidin or fluorescein-anti-mouse IgG (Sigma). Fluorescence associated with the polymer nanotube fraction will provide a measure of the conjugation.

The chemiluminescent signal from the biotin, streptavidin or anti-TSH conjugated enzyme-loaded polymer nanotubes will be assessed. The degree of enhancement will be assessed by comparison of the chemiluminescent signal-dilution curve of the enzyme-loaded polymer nanotube preparation with a standard curve for soluble enzyme.

The enzyme immunoassay for TSH (e.g., the polyclonal anti-TSH antibody in the DPC Immulite Third Generation TSH assay (cat # L2KTS2) will be modified for use with an antibody enzyme-loaded polymer nanotube conjugate. The single level third generation low control and dilutions of the control (DPC cat # LTGCM) will be assayed in duplicate using the unmodified immunoassay and the modified assay for purposes of comparison.

The alkaline phosphatase, label will be measured using AMPPD or using the DPC Chemiluminescent substrate (DPC cat # L2SUBM). Peroxidase and firefly luciferase labels will be measured. Light measurement will be made using a Berthold single tube luminometer (tube assays) or via imaging of reactions performed in microwells using the NightOwl CCD luminometer.

A nucleic acid test that quantitates the mRNA transcripts of prostate specific antigen will be compared to a novel polymer-nanotube conjugated method. PSA mRNA will be detected by northern blot probed by PSA-mRNA specific oligonucleotides (Meng et al., 2002) linked to biotin. Biotin-linked probes will then bind to either alkaline phosphatase linked to streptavidin or alternatively, to the novel streptavidin enzyme-loaded polymer nanotube. Alkaline phosphatase, horseradish peroxidase and firefly luciferase will be measured.

Example 2

Measurement of Enzyme Loading on Nanostructures Constructed by Layer-layer Techniques This high degree of enzyme loading can be estimated for carbon nanotubes. For example, the carbon nanotubes can be carboxylated single-walled carbon nanotubes of average diameter of 5 nm and average length of 1 μm (Sigma-Aldrich, Cat No. 652490). The surface density of each monolayer of electrostatically assembled alkaline phosphatase on a carbon nanotubes is estimated to be $2.6 \times 10^{14}$ enzyme molecules per $cm^2$. Because a 5 nm diameter single-walled carbon nanotube of 1 μm in length has a surface area of $1.57 \times 10^{-10}$ $cm^2$, each electrostatically assembled monolayer can be comprised of approximately 40,820 enzyme molecules. A four enzyme layer structure would have approximately four-times the loaded enzyme, approximately 160,000 enzyme molecules. This high degree of loading will directly translate into a significantly greater number of enzyme tags per binding event than currently exists in any immunoassays or nucleic acid assays.

Example 3

Exemplary Layer-by-layer Assembly of Alkaline Phosphatase

Carboxylated carbon nanotubes in solution are adjusted to pH 8.0, and then PDDA is absorbed to the single-walled carbon nanotube surface (SWCNT) by sonicating 0.5 mg $ml^{-1}$ of SWCNT in a 0.5 M NaCl solution containing 1 mg $mL^{-1}$ PDDA for 5 minutes. This sonication is followed by shaking at regular intervals for 20 minutes. The PDDA-coated SWCNTs are then centrifuged at 9000 rpm for 15 minutes to remove supernatant. One milliliter of deionized water is then added to resuspend the PDDA-coated SWCNTs. This procedure of centrifugation followed by resuspension in deionized water is repeated three times. The resultant SWCNT complex is coated with PDDA resulting in a net positive charge. Next, a layer of negatively charged ALP molecule is added. The procedure is similar to that used for PDDA absorption. ALP (alkaline phosphatase) (1 mg $mL^{-1}$, pH 8.0) is absorbed to the SWCNT surface by sonicating in 0.5 M NaCl solution for 5 minutes. The sonication is followed by regular shaking at 20 minute intervals followed by centrifugation and resuspension in deionized water as per the PDDA absorption and washing procedure. Additional layers of PDDA alternated with ALP will be electrostatically deposited with a final core to surface assembly abbreviated as: SWCNT-(PDDA-ALP)$_N$-PDDA; where N is the number of layered PDDA-ALP complexes. This final structure will be capped with streptavidin by absorbing negatively charged streptavidin (0.25 mg mL$^{-1}$, pH 7.5) to the outermost PDDA layer for a final complex of SWCNT-(PDDA-ALP)$_N$-PDDA-streptavidin.

The fabricated CNT-(PDDA/ALP)N-PDDA-streptavidin labels (N=1 to 10) in 0.1 M phosphate buffer (pH 7.4) will be assessed for alkaline phosphatase activity based on standard methods with chemiluminescent 1,2-dioxetane substrate. Results will be referenced to a standard curve generated by measuring light units generated by free alkaline phosphatase (Cat. No. 31391; Pierce Biotech; Rockord, Ill.) from a concentration range of $1 \times 10^{-16}$ to $1 \times 10^{-12}$ M. In brief, either 5 µl of free alkaline phosphatase or 5 µl of (50 mg/mL CNT-(PDDA/ALP)N-PDDA-streptavidin) label will be added to 100 µl of luminescence solution composed of 0.4 mM 1,2-dioxetane substrate; 0.05 M carbonate; 1 mM MgCl$_2$; at pH 9.5. After a 20 minute incubation at room temperature, the chemiluminescent signal will be measured on a luminometer using a 10-second average output. A standard curve will be generated from five different concentrations ($1 \times 10^{-16}$ to $1 \times 10^{-12}$ M) of free alkaline phosphatase, each in duplicate. This standard curve will be used to estimate the amount of enzymatically active immobilized enzyme per gram of carbon nanotube.

Basic kinetic data on immobilized alkaline phosphates will be obtained by conventional methods of assessing substrate Vmax and Km values. 5 µl of label (50 mg/mL CNT-(PDDA/ALP)N-PDDA-streptavidin) will be added to 100 µl of luminescence solutions composed of 0.05 M carbonate and 1 mM MgCl2 at pH 9.5. In addition, the luminescence solutions will containing varying concentrations of 1,2-dioxetane substrate from 0.1 mM to 1.0 mM. After a fixed time of incubation at room temperature (2 to 30 minutes), the chemiluminescent signal will be measured on a luminometer using a 10-second average output.

The 1,2-dioxetane-based chemiluminescent substrates that have been previously characterized for alkaline phosphatase catalysed luminescence will be used. For example, 1,2-dioxetane-based substrates that can be used are CSPD® (Disodium 3-(4-metho xyspiro{1,2-dioxetane-3,2-(5-chloro)tricyclo[3.3.1.13,7]decan}-4-yl)phenyl phosphate) and CDP Star® (Disodium 4-chloro-3-(methoxyspiro{1,2-dioxetane-3,2-(5-chloro)tricycle[3.3.1.13,7]decan}-4-yl)phenyl phosphate) which are commercially available from Applied Biosystems-Tropix. (Bedford, Mass.).

Based on the estimation of enzymatically active immobilized enzyme, the approximate number of alkaline phosphatase molecules immobilized per layer will be calculated, as well as the corresponding surface density. The surface density of each monolayer of electrostatically assembled alkaline phosphatase on a carbon nanotube has been estimated to be $2.6 \times 10^{14}$ enzyme molecules per cm$^2$. Since these studies will utilize a 5 nm diameter single-walled carbon nanotube of 1 µm in length that has a surface area of $1.57 \times 10^{-10}$ cm$^2$, each fabricated CNT-(PDDA/ALP)$_1$-PDDA-streptavidin label molecule will have a monolayer of approximately 40,820 enzyme molecules. Similarly, A four enzyme layer structure would have approximately four-times the loaded enzyme, ~160,000 enzyme molecules.

Alkaline phosphatase assembled on carbon nanotubes have been used as labels in conjunction with streptavidin-coated magnetic beads for the isolation and detection of nucleic acids and proteins (Munge et al. *Anal Chem* 2005;77: 4662-6). These previously established methods for performing hybridization assays on a magnetic bead Dynal MPC platform (Dynalbiotech) will be adapted. Hybridization complexes will be formed on streptavidin coated magnetic beads as previously described with the intention of assembling a complex with the orientation of: (magnetic bead)-(DNA probe 1)-(target nucleic acid)-(DNA probe 2)-(ALP-CNT complex).

In brief, 5 µL of streptavidin-coated magnetic beads (CM01N; Bangs Laboratories, Inc.; Fishers, Ind.) at 10 µg/µL are added to a 1.5 mL centrifuge tube. The beads are washed twice with 95 µL of TTL buffer (100 mM Tris-HCl, pH 8.0, 0.1% Tween 20, and 1 M LiCl) and suspended in 21 µL of TTL buffer. Next, ~0.5 nmoles of biotin DNA probe 1 is added to the beads. This mixture is incubated at 25° C. for 20 minutes with gentle mixing. Next, the DNA-coated magnetic beads are washed twice with 95 µL of TTA buffer (250 mM Tris-HCl, 0.1% Tween 20, and 10% BSA) and suspended in 45 µL of the hybridization buffer (750 mM NaCl, 150 mM sodium citrate). Next, the target DNA is added and incubating at 25° C. for 20 minutes with gentle mixing. The target conjugated magnetic beads are washed twice with 95 µL of TTA and then suspended in 45 µL of hybridization buffer. This is followed by adding ~0.5 nmoles of the biotin DNA 2 probe and incubating at 25° C. for 20 minutes with gentle shaking. This hybridization is followed by magnetic separation and two washes with 95 µL of TTL buffer. Finally, the bead hybridized complex is resuspended in 95 µL of TTL buffer and 5 µL of the ALP-CNT label (0.05 mg/mL) is added and the mixture is incubated at 25° C. for 20 minutes. This is followed by magnetic separation and dual washing with the TTL buffer. The captured complex is resuspended in 50 µL luminescence assay buffer that lacks chemiluminescent substrate (0.05 M carbonate; 1 mM MgCl$_2$; at pH 9.5).

The temperature and salt concentration will be varied during the hybridization of target DNA as well as for DNA probe 2. Temperature will be varied from 25° C. to 50° C. for each hybridization step as well as target DNA and DNA probe 2. The salt concentration will be varied by adjusting the NaCl concentration from 250 mM to 1250 mM. Both temperature and salt optimizations will be performed in parallel with the non-specific, scramble probe as well as a blank that has no target probe.

The optimized CNT-(PDDA/ALP)$_N$-PDDA-streptavidin labels will be assessed for chemiluminescent alkaline phosphatase activity in the context of the magnetic bead capture assay. In brief, 50 µl of the label complexed with nucleic acid hybridized bead will be added to 50 µl of luminescence solution with concentrated 1,2-dioxetane substrate to give a final reaction mix with 0.4 mM 1,2-dioxetane, 0.05 M carbonate, 1 mM MgCl$_2$ at pH 9.5. After incubation for time and temperature defined by specific aim 1, the chemiluminescent signal will be measured on a luminometer using a 10-second average output.

The assay will be used for the detection of the PSA marker in dilutions of purified analyte as well as in complex biologic matrices. The purified analyte will be PSA mRNA and its corresponding reverse transcribed cDNA. The biologic matrices that will be used include mRNA and total RNA from prostate cancer cell lines, blood specimens with prostate cancer cells, and lymph nodes with metastatic prostate cancer cells.

In addition, PSA mRNA will be also be directly assayed by the ALP-CNT-OLIGO capture assay. PSA mRNA that has been prepared by expression construct will be purified by oligo(dT) and then quantified by UV-vis as well as quantitative real-time RT-PCR.

The ALP-CNT-OLIGO will also be characterized for the detection of PSA mRNA and cDNA within the context of a biologic matrix. Total RNA will be extracted from prostate cancer cell lines, and blood spiked with prostate cancer cells. The total RNA extract will be assayed untreated or alternatively will be reverse transcribed into cDNA and then assayed. Samples will be run in parallel with positive and negative controls. The positive control to be run in parallel will be the synthetic target. There will be several negative controls used: i) blank, no target DNA; ii) scramble target DNA; iii) total RNA and cDNA from negative control cell line. The total RNA and corresponding cDNA from 293 human kidney cells will be used as the negative control.

One alternative to layer-by-layer assembly on carbon nanotubes would be the use of either polystyrene nanoparticles or glass colloids. Indeed, the layer-by-layer process is dependent on assembly on a charged surface and is compatible with many different materials. Spherical particles have been used previously in layer-by-layer assemblies of fluorescent and bioluminescent molecules and are suitable for the assembly of chemiluminescent enzymes such as alkaline phosphatase.

What is claimed:

1. A method for determining the concentration of an analyte in a sample, said method comprising:
    contacting the sample with a nanostructure, the nanostructure being associated with a luminescent label and comprising an enhancer that comprises a polymer and that creates a nanoenvironment for modulating said luminescent label, wherein said enhancer is loaded into or onto said nanostructure, or is otherwise associated with said nanostructure;
    the nanostructure having binding specificity for the analyte;
    generating luminescence, wherein said luminescence is increased by said enhancer; without a concomitant increase in background luminescence and,
    measuring the amount of luminescence, wherein said amount of luminescence correlates to the concentration of said analyte in said sample.

2. The method of claim 1, wherein said method further comprises a step of removing unbound nanostructure from the sample prior to the generation of luminescence.

3. The method of claim 1, wherein the binding specificity for the analyte is imparted to the nanostructure by a binding moiety conjugated to the nanostructure.

4. The method of claim 3 wherein said binding moiety is an oligonucleotide, peptide, ligand, small molecule, hapten, or antibody.

5. The method of claim 1 wherein said luminescent label generates fluorescence.

6. The method of claim 1 wherein said luminescent label is an enzymatic label.

7. The method of claim 1 wherein said luminescent label is a chemical label.

8. The method of claim 1 wherein said luminescent label comprises a fluorescent label, a chemiluminescent label, a bioluminescent label, or a combination thereof.

9. The method of claim 1 wherein said luminescent label is a fluorophore.

10. The method of claim 1 wherein said luminescent label is alkaline phosphatase.

11. The method of claim 10 wherein said enhancer is a polymer, and said polymer is poly[vinylbenzyl(benzyldimethylammonium) chloride].

12. The method of claim 10 wherein said enhancer is a polymer, and said polymer is a polyhydroxyacrylate, polyvinyl carbamate, methacrylate, polyvinylalkylether, polyethylenesulfonic acid, polyacrylamideomethylpropanesulfonic acid, polyvinyl alcohol, polyvinylalkylpyrrolidinone, polyvinylalkyloxazolidones, BSA, or nylon.

13. The method of claim 1 wherein said luminescent label is a peroxidase enzyme.

14. The method of claim 13 wherein said enzyme is horseradish peroxidase.

15. The method of claim 13 wherein said enhancer is a polymer, and said polymer is hydroxypropyl methyl cellulose, hydroxyethyl cellulose and hydroxybutyl methyl cellulose.

16. The method of claim 1 wherein said luminescent label is a luciferase.

17. The method of claim 16 wherein said luciferase is firefly luciferase.

18. The method of claim 16 wherein said enhancer is a polymer, and said polymer is polyethylene glycol, polyvinylpyrrolidone, or dextran.

19. The method of claim 1 wherein said nanostructure comprises carbon or silica.

20. The method of claim 19 wherein said nanostructure is a carbon or silica nanotube.

21. The method of claim 1 further comprising the step of providing to the sample a labeled detector probe having binding specificity for said analyte, wherein the nanostructure has binding specificity for said labeled detector probe.

22. The method of claim 21 wherein said analyte is nucleic acid and said labeled detector probe comprises a nucleic acid sequence complementary to said analyte.

23. The method of claim 22 wherein said nucleic acid is RNA.

24. The method of claim 22 wherein said nucleic acid is DNA.

25. The method of claim 21 wherein said analyte is a protein and said labeled detector probe comprises an antibody having binding specificity for said protein.

26. The method of claim 1 wherein said analyte is prostate specific antigen mRNA.

27. The method of claim 1 wherein said analyte is thyrotropin.

28. The method according to claim 1 wherein said enhancer is used to fabricate said nanostructure.

29. The method according to claim 1 wherein said enhancer is covalently bound to the nanostructure.

30. The method according to claim 1 wherein said enhancer is assembled onto the nanostructure by electrostatic assembly.

31. The method according to claim 1 wherein said nanostructure comprises a scaffold and at least two layers that are on said scaffold, wherein one of said layers comprises said luminescent label.

32. The method according to claim 31 wherein a second of said at least two layers comprises said enhancer, and wherein said second layer is adjacent to said layer that comprises said luminescent label.

33. A method for detecting the absence or presence of an analyte in a sample, said method comprising:
    contacting the sample with a nanostructure that is associated with a luminescent label, the nanostructure having binding specificity for the analyte and comprising an enhancer that comprises a polymer and that creates a nanoenvironment for modulating said luminescent label, wherein said enhancer is loaded into or onto said nanostructure, or is otherwise associated with said nanostructure; and, detecting the presence or absence of luminescence wherein the presence of luminescence wherein said luminescence, when present, is increased by said enhancer without a concomitant increase in background luminescence, and indicates that the analyte is present in the sample.

34. A method for determining the concentration of an analyte in a sample, said method comprising:

contacting the sample with a nanostructure, the nanostructure being associated with a luminescent label and comprising an enhancer that creates a nanoenvironment for modulating said luminescent label, wherein said nanostructure is fabricated from said enhancer, and wherein said enhancer is poly(lactic acid-co-glycolic acid), poly(acrylic acid)-poly (pyrene methanol), polypyrrole, poly (3-methylthiophene), polyaniline, polyacrylonitrile, poly(p-phenylene), poly(3,4-ethylenedioxythiophene), polyacrylonitrile, poly(L-lactic acid)-polycaprolactone, polystyrene-block-poly(2-cinnamoylethyl methacrylate), polystyrene-block-poly(2-cinnamoylethyl methacrylate)-block-poly(tert-butyl acrylate), peptide-amphiphile, dendrimer, bolaform glucosamide, polystyrene, polycarbonate, polymethacrylate, polyvinylchloride, polyethylene terephthalate, polyamide, polyurethane, polylactic acid, polycaprolactone, polyethylene glycol, polylactide-co-glycolide, polyethylene-co-vinyl acetate, polyethylene co-vinyl alcohol, polyethylene oxide, collagen, amphiphilic poly(2-methyloxazoline-block-dimethylsiloxane-block-2-methyloxazoline)(PMOXA-b-PDMS-b-PMOXA) ABA triblock copolymers, poly(thiophene), polyetherketone, polyallylamine, polyethyleneimine, poly(iminohexamethylene), polytetrafluoroethylene, poly(oxy-1,4,-phenyleneoxyl-1,4-phenylenecarbonyl-1,4-phenylene), polyvinylidene fluoride, polymethyl methacrylate, polystyrene, poly[vinylbenzyl(benzyldimethylammonium) chloride], polyhydroxyacrylate, polyvinyl carbamate, methacrylate, polyvinylalkylether, polyethylenesulfonic acid, polyacrylamideomethylpropanesulfonic acid, polyvinyl alcohol, polyvinylalkylpyrrolidinone, polyvinylalkyloxazolidones, BSA, nylon, alkyl hydroxyalkyl cellulose, hydroxyalkyl cellulose, polyethylene glycol, polyvinylpyrrolidone, dextran, or blends or composites thereof;

the nanostructure having binding specificity for the analyte;

generating luminescence, wherein said luminescence is modulated by said enhancer; and, measuring the amount of luminescence, wherein said amount of luminescence correlates to the concentration of said analyte in said sample.

35. The method of claim 34 wherein said luminescent label generates fluorescence.

36. The method of claim 34 wherein said luminescent label is an enzymatic label.

37. The method of claim 34 wherein said luminescent label is a chemical label.

38. The method of claim 34 wherein said luminescent label comprises a fluorescent label, a chemiluminescent label, a bioluminescent label, or a combination thereof.

39. The method of claim 34 wherein said luminescent label is a fluorophore.

40. The method of claim 34 wherein said luminescent label is alkaline phosphatase.

41. The method of claim 40 wherein said enhancer is a polymer, and said polymer is poly[vinylbenzyl(benzyldimethylammonium) chloride].

42. The method of claim 40 wherein said enhancer is a polymer, and said polymer is a polyhydroxyacrylate, polyvinyl carbamate, methacrylate, polyvinylalkylether, polyethylenesulfonic acid, polyacrylamideomethylpropanesulfonic acid, polyvinyl alcohol, polyvinylalkylpyrrolidinone, polyvinylalkyloxazolidones, BSA, or nylon.

43. The method of claim 34 wherein said luminescent label is a peroxidase enzyme.

44. The method of claim 43 wherein said enzyme is horseradish peroxidase.

45. The method of claim 43 wherein said enhancer is a polymer, and said polymer is hydroxypropyl methyl cellulose, hydroxyethyl cellulose and hydroxybutyl methyl cellulose.

46. The method of claim 34 wherein said luminescent label is a luciferase.

47. The method of claim 46 wherein said luciferase is firefly luciferase.

48. The method of claim 46 wherein said enhancer is a polymer, and said polymer is polyethylene glycol, polyvinylpyrrolidone, or dextran.

49. The method of claim 34, wherein the binding specificity for the analyte is imparted to the nanostructure by a binding moiety conjugated to the nanostructure.

50. The method of claim 49 wherein said binding moiety is an oligonucleotide, peptide, ligand, small molecule, hapten, or antibody.

51. The method according to claim 34 wherein said nanostructure comprises carbon or silica.

52. The method of claim 51 wherein said nanostructure is a carbon or silica nanotube.

53. The method of claim 34 further comprising the step of providing to the sample a labeled detector having binding specificity for said analyte, wherein the nanostructure has binding specificity for said labeled detector probe.

54. The method of claim 53 wherein said analyte is nucleic acid and said labeled detector probe comprises a nucleic acid sequence complementary to said analyte.

55. The method of claim 53 wherein said analyte is a protein and said labeled detector probe comprises an antibody having binding specificity for said protein.

* * * * *